(12) United States Patent
Masuyama et al.

(10) Patent No.: US 8,173,353 B2
(45) Date of Patent: May 8, 2012

(54) SULFONIUM COMPOUND

(75) Inventors: Tatsuro Masuyama, Toyonaka (JP); Junji Shigematsu, Ibaraki (JP); Hanwoo Park, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 231 days.

(21) Appl. No.: 12/729,550

(22) Filed: Mar. 23, 2010

(65) Prior Publication Data

US 2010/0248135 A1    Sep. 30, 2010

(30) Foreign Application Priority Data

Mar. 26, 2009  (JP) .................................. 2009-075996

(51) Int. Cl.
*G03F 7/004* (2006.01)
*C07C 309/12* (2006.01)

(52) U.S. Cl. .................. 430/270.1; 430/921; 430/922; 560/129; 560/150; 562/42; 562/100; 562/109; 562/114

(58) Field of Classification Search ............... 430/270.1, 430/921, 922; 560/129, 150; 562/42, 100, 562/109, 114
See application file for complete search history.

(56) References Cited

U.S. PATENT DOCUMENTS

| 2003/0194639 A1 | 10/2003 | Miya et al. | |
|---|---|---|---|
| 2008/0085469 A1* | 4/2008 | Ohsawa et al. | 430/286.1 |
| 2009/0061358 A1* | 3/2009 | Ohashi et al. | 430/286.1 |

* cited by examiner

*Primary Examiner* — John Chu

(74) *Attorney, Agent, or Firm* — Birch, Stewart, Kolasch & Birch, LLP

(57) ABSTRACT

The present invention provides a sulfonium compound represented by the formula (I):

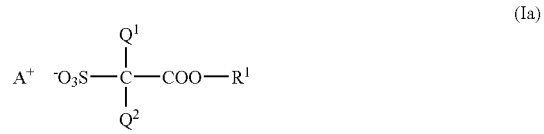

(Ia)

wherein $Q^1$ and $Q^2$ each independently represent a fluorine atom or a C1-C6 perfluoroalkyl group, R1 represents a C5-C42 organic group having a β-ketoester structure and $A^+$ represents an organic counter ion, and a chemically amplified photoresist composition comprising the above-mentioned sulfonium compound and a resin comprising a structural unit having an acid-labile group and being insoluble or poorly soluble in an aqueous alkali solution but becoming soluble in an aqueous alkali solution by the action of an acid.

11 Claims, No Drawings

SULFONIUM COMPOUND

This nonprovisional application claims priority under 35 U.S.C. §119(a) on Patent Applications No. 2009-075996 filed in JAPAN on Mar. 26, 2009, the entire contents of which are hereby incorporated by reference.

FIELD OF THE INVENTION

The present invention relates to a novel sulfonium compound suitable for an acid generator.

BACKGROUND OF THE INVENTION

A chemically amplified positive resist composition used for semiconductor microfabrication employing a lithography process contains an acid generator comprising a compound generating an acid by irradiation.

U.S. 2003/0194639 A1 discloses a sulfonium compound represented by the following formula:

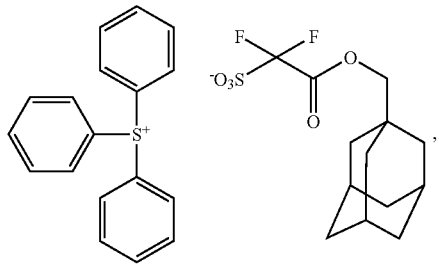

and a chemically amplified resist composition containing the same as the acid generator.

SUMMARY OF THE INVENTION

An object of the present invention is to provide a novel sulfonium compound suitable for an acid generator.

The present invention relates to the followings:

<1> A sulfonium compound represented by the formula (I):

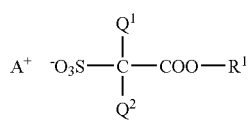

(Ia)

wherein $Q^1$ and $Q^2$ each independently represent a fluorine atom or a C1-C6 perfluoroalkyl group, R1 represents a C5-C42 organic group having a β-ketoester structure and $A^+$ represents an organic counter ion;

<2> The sulfonium compound according to <1>, wherein $R^1$ is a group represented by the formula (Ib):

wherein $R^2$ represents a C1-C12 divalent hydrocarbon group and $R^3$ represents a C1-C24 hydrocarbon group which may have one or more substituents, and —$CH_2$— in the C1-C24 hydrocarbon group may be replaced by —NH—, —CO— or —O—, and —CH= in the C1-C24 hydrocarbon group may be replaced by —N=;

<3> The sulfonium compound according to <2>, wherein $R^2$ is a methylene group, an ethylene group, a trimethylene group or a tetramethylene group;

<4> The sulfonium compound according to <2> or <3>, wherein the substituent in $R^3$ is a halogen atom, a hydroxyl group, a cyano group, —$OR^4$—, —CO—$OR^4$, —O—CO—$R^4$, —$SO_2R^4$ or —O—$SO_2$—$R^4$ wherein $R^4$ represents a C1-C6 hydrocarbon group;

<5> The sulfonium compound according to any one of <1> to <4>, wherein $Q^1$ and $Q^2$ each independently represent a fluorine atom or a trifluoromethyl group;

<6> The sulfonium compound according to any one of <1> to <5>, wherein the organic counter ion is a cation represented by the formula (IXz):

wherein $P^a$, $P^b$ and $P^c$ each independently represent a C1-C30 alkyl group which may be substituted with at least one selected from the group consisting of a hydroxyl group, a C1-C12 alkoxy group and a C3-C12 cyclic hydrocarbon group, or a C3-C30 cyclic hydrocarbon group which may be substituted with at least one selected from the group consisting of a hydroxyl group, a halogen atom and a C1-C12 alkoxy group;

<7> The sulfonium compound according to any one of <1> to <5>, wherein the organic counter ion is a cation represented by the formula (IIIa):

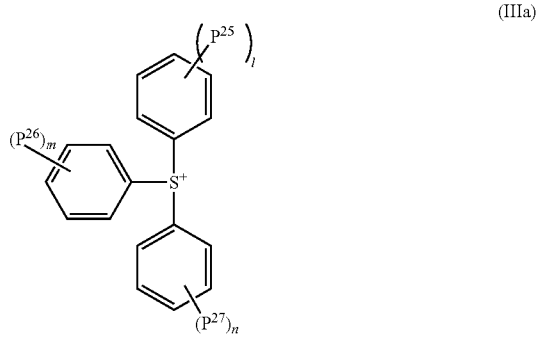

wherein $P^{25}$, $P^{26}$ and $P^{27}$ are independently in each occurrence a hydroxyl group, a halogen atom, a C1-C12 alkyl group, a C1-C12 alkoxy group or a C3-C12 cyclic hydrocarbon group, and the C3-C12 cyclic hydrocarbon group may be substituted with a halogen atom, a hydroxyl group or a C1-C12 alkoxy group, and l, m and n each independently represent an integer of 0 to 5;

<8> A chemically amplified photoresist composition comprising a sulfonium compound according to any one of <1> to <7> and a resin comprising a structural unit having an acid-labile group and being insoluble or poorly soluble in an aqueous alkali solution but becoming soluble in an aqueous alkali solution by the action of an acid;

<9> The chemically amplified photoresist composition according to <8>, wherein the composition further contains a basic compound;

<10> A process for production of a sulfonium compound represented by the formula (Ia):

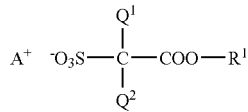

wherein $Q^1$ and $Q^2$ each independently represent a fluorine atom or a C1-C6 perfluoroalkyl group, R1 represents a C5-C42 organic group having a β-ketoester structure and $A^+$ represents an organic counter ion, which comprises reacting a compound represented by the formula (VI):

$$Z—R^1 \tag{VI}$$

wherein $R^1$ is the same as defined above, and Z represents a halogen atom, with a salt represented by the formula (VII):

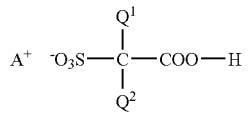

wherein $Q^1$, $Q^2$ and $A^+$ are the same as defined above;

<11> A process for production of a sulfonium compound represented by the formula (Ia):

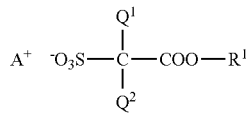

wherein $Q^1$ and $Q^2$ each independently represent a fluorine atom or a C1-C6 perfluoroalkyl group, R1 represents a C5-C42 organic group having a β-ketoester structure and $A^+$ represents an organic counter ion, which comprises reacting a compound represented by the formula (VIII):

$$A^+L^- \tag{VIII}$$

wherein $A^+$ is the same as defined above, and $L^-$ represents $F^-$, $Cl^-$, $Br^-$, $I^-$, $BF_4^-$, $AsF_6^-$, $SbF_6^-$, $PF_6^-$ or $ClO_4^-$, with a salt represented by the formula (IX):

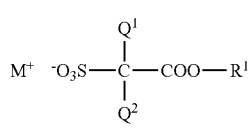

wherein $Q^1$, $Q^2$ and $R^1$ are the same as defined above and $M^+$ is $Li^+$, $Na^+$ or $K^+$.

DESCRIPTION OF PREFERRED EMBODIMENTS

The sulfonium compound is represented by the formula (I):

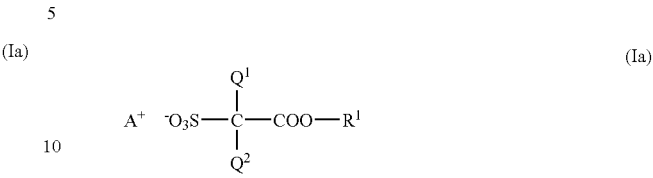

wherein $Q^1$ and $Q^2$ each independently represent a fluorine atom or a C1-C6 perfluoroalkyl group, $R^1$ represents a C5-C42 organic group having a β-ketoester structure and $A^+$ represents an organic counter ion (hereinafter, simply referred to as the sulfonium compound (Ia)).

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. It is preferred that $Q^1$ and $Q^2$ each independently represent a fluorine atom or a trifluoromethyl group, and it is more preferred that $Q^1$ and $Q^2$ represent fluorine atoms.

Examples of the C5-C42 organic group having a β-ketoester structure include a group represented by the formula (I-1):

$$R^2—X^1—R^3 \tag{I-1}$$

wherein $R^2$ represents a C1-C12 divalent hydrocarbon group and $R^3$ represents a C1-C24 hydrocarbon group which may have one or more substituents, and —$CH_2$— in the C1-C24 hydrocarbon group may be replaced by —NH—, —CO— or —O—, and —CH= in the C1-C24 hydrocarbon group may be replaced by —NH=, $X^1$ represents *—CO—$CR^aR^b$—CO—O— or *—O—CO—$CR^aR^b$—CO— wherein $R^a$ and $R^b$ each independently represent a hydrogen atom, or $R^a$ represents a hydrogen atom and $R^b$ and $R^3$ are bonded each other to form a C3-C24 ring, or $R^a$, $R^b$ and $R^3$ are bonded each other to form a C3-C24 ring, and * is a binding site for $R^2$.

Examples of the group represented by the formula (I-1) wherein $R^a$ and $R^b$ are hydrogen atoms include a group represented by the formula (Ib) and a group represented by the formula (Ic):

$$—R^2—CO—CH_2—COO—R^3 \tag{Ib}$$

$$—R^2—O—CO—CH_2—CO—R^3 \tag{Ic}$$

wherein $R^2$ and $R^3$ are the same as defined above.

Examples of the C1-C12 divalent hydrocarbon group in $R^2$ include a C1-C12 divalent linear aliphatic hydrocarbon group, a C3-C12 divalent branched chain aliphatic hydrocarbon group, a C3-C12 divalent cyclic hydrocarbon group and a group formed by combining two or more groups among them. Examples of the divalent linear or branched chain aliphatic hydrocarbon group include a C1-C12 alkylene group such as a methylene group, an ethylene group, a propylene group, a butylene group, a pentamethylene group, a hexamethylene group, a heptamethylene group, an octamethylene group, a nonamethylene group, a decamethylene group, an undecamethylene group, and a dodecamethylene group. Examples of the divalent cyclic hydrocarbon group include the followings:

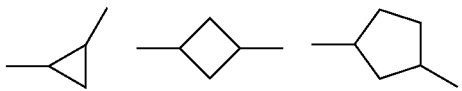

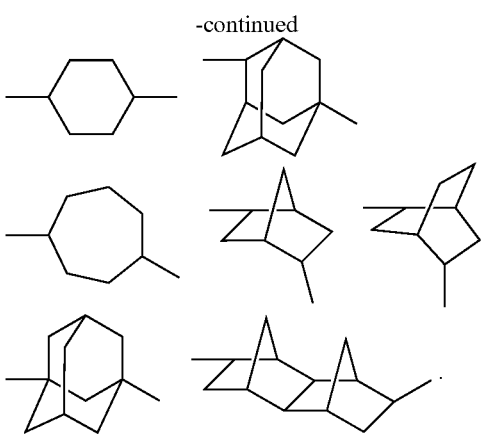

Examples of the group formed by combining two or more groups among the C1-C12 divalent linear aliphatic hydrocarbon group, the C3-C12 divalent branched chain aliphatic hydrocarbon group and the C3-C12 divalent cyclic hydrocarbon group include the followings:

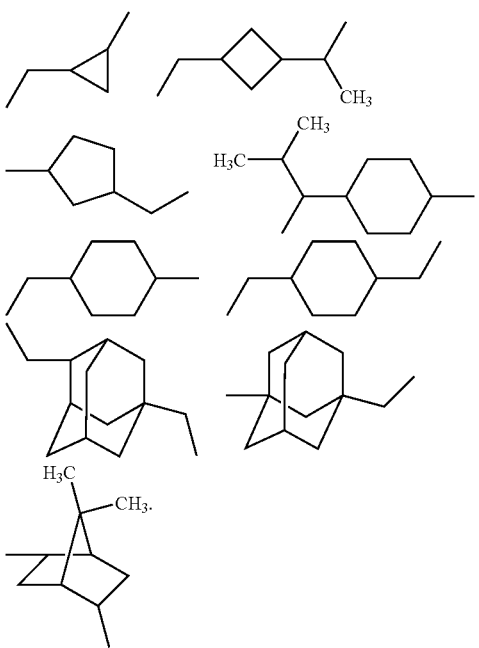

Examples of the C1-C24 hydrocarbon group in $R^3$ include a C1-C24 linear aliphatic hydrocarbon group, C3-C24 branched chain aliphatic hydrocarbon group, a C3-C24 alicyclic hydrocarbon group, a C5-C24 aromatic hydrocarbon group and a C6-C24 aralkyl group. The C1-C24 hydrocarbon group which may have one or more substituents, and —$CH_2$— in the C1-C24 hydrocarbon group may be replaced by —NH—, —CO— or —O—, and —CH= in the C1-C24 hydrocarbon group may be replaced by —NH=. Examples of the substituents include a halogen atom such as a fluorine atom, a hydroxyl group, a cyano group, —$OR^4$—, —CO—$OR^4$, —O—CO—$R^4$, —$SO_2R^4$ and —O—$SO_2$—$R^4$ wherein $R^4$ represents a C1-C6 hydrocarbon group. Examples of the C1-C6 hydrocarbon group in $R^4$ include a C1-C6 linear aliphatic hydrocarbon group such as a methyl group, an ethyl group, a propyl group, a butyl group, a pentyl group and a hexyl group, a C3-C6 branched chain aliphatic hydrocarbon group such as an isopropyl group, a sec-butyl group, a tert-butyl group and a methylpentyl group, a C3-C6 alicyclic group such as a cyclopropyl group, a cyclobutyl group, a cyclopentyl group and a cyclohexyl group, and a phenyl group.

Examples of the C1-C24 linear aliphatic hydrocarbon group include a C1-C24 linear alkyl group such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a henicosyl group, a docosanyl group, a tricosanyl group, a tetracosanyl group, a pentacosanyl group, a hexacosanyl group, a heptacosanyl group, an octacosanyl group, a nonacosanyl group and a triacontanyl group, and a methyl group, an ethyl group, a propyl group and a butyl group are preferable.

Examples of the C3-C24 branched chain aliphatic hydrocarbon group include a C3-C24 branched chain alkyl group such as an isopropyl group, a sec-butyl group, a tert-butyl group, a methylpentyl group, an ethylpentyl group, a methylhexyl group, an ethylhexyl group, a propylhexyl group and a tert-octyl group, and an isopropyl group, a sec-butyl group, a tert-butyl group and an ethylhexyl group are preferable.

Examples of the C3-C24 alicyclic hydrocarbon group include the followings:

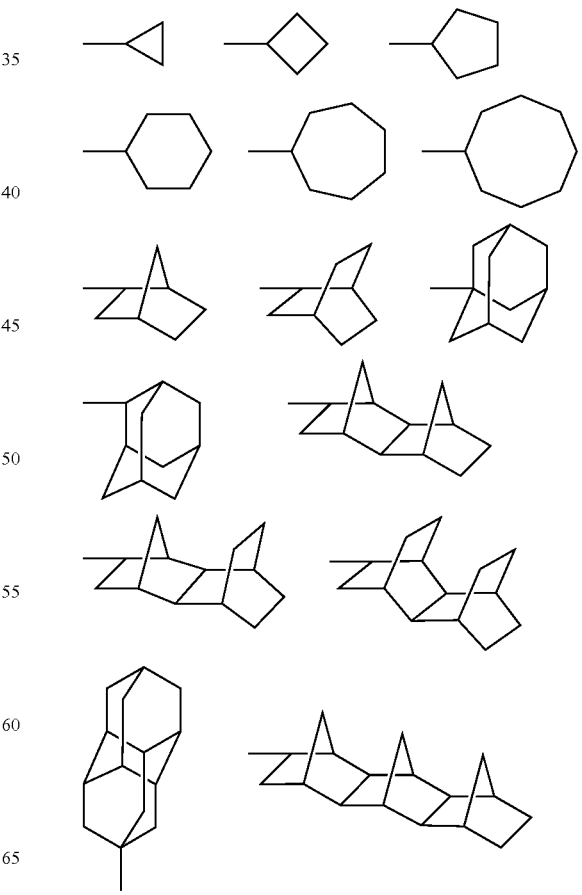

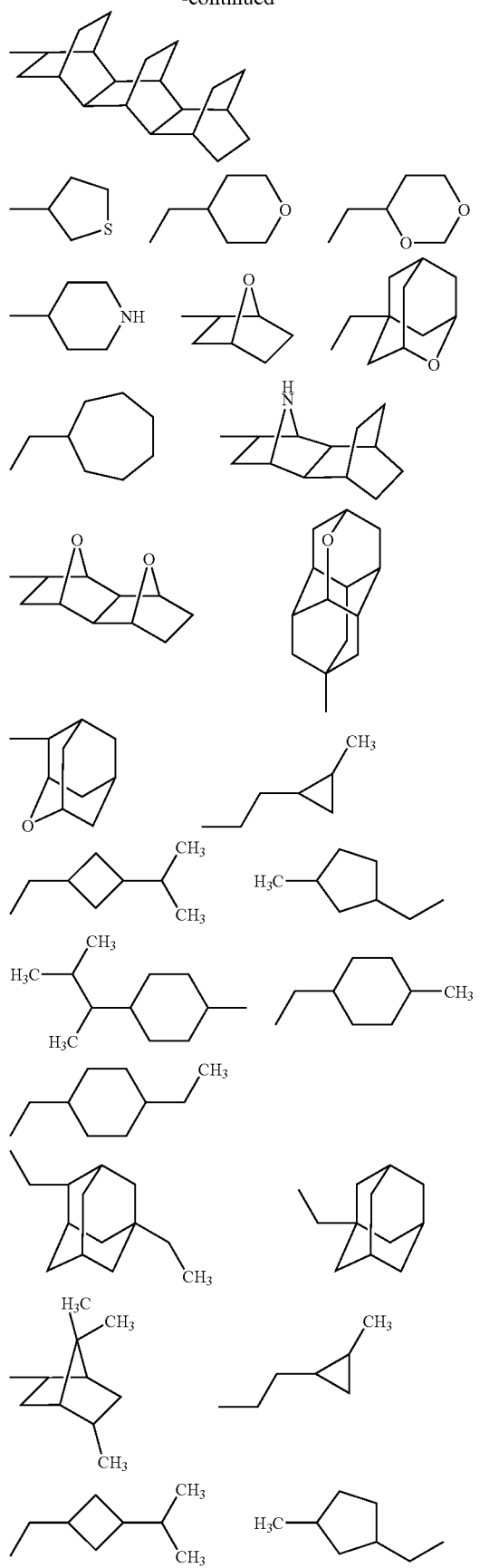
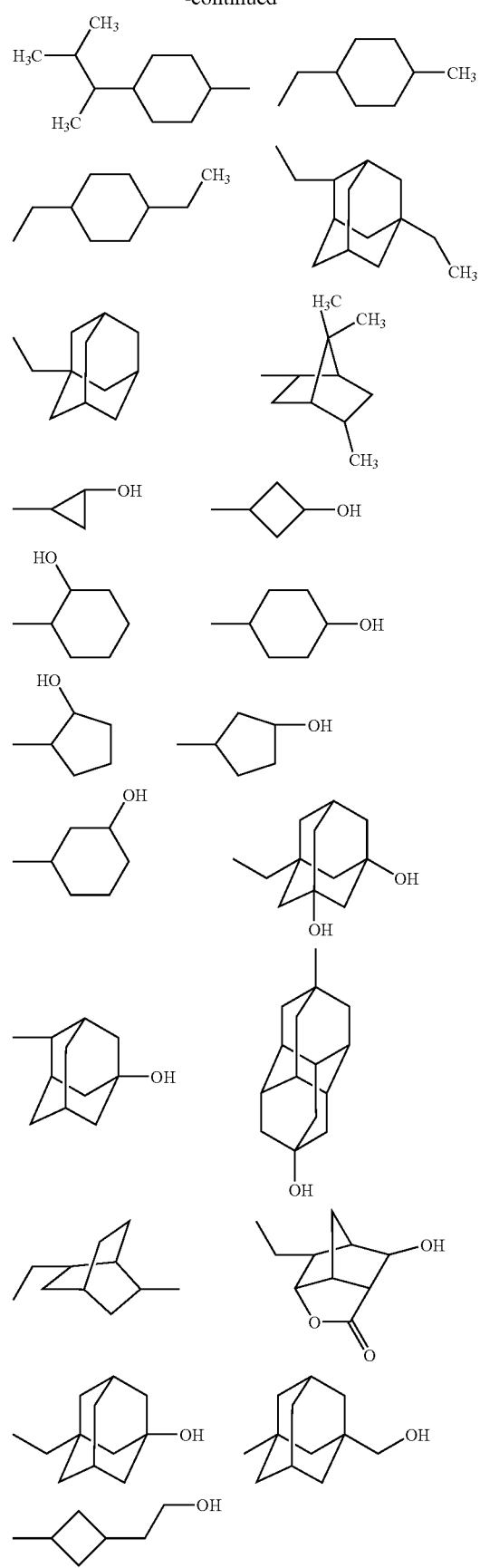

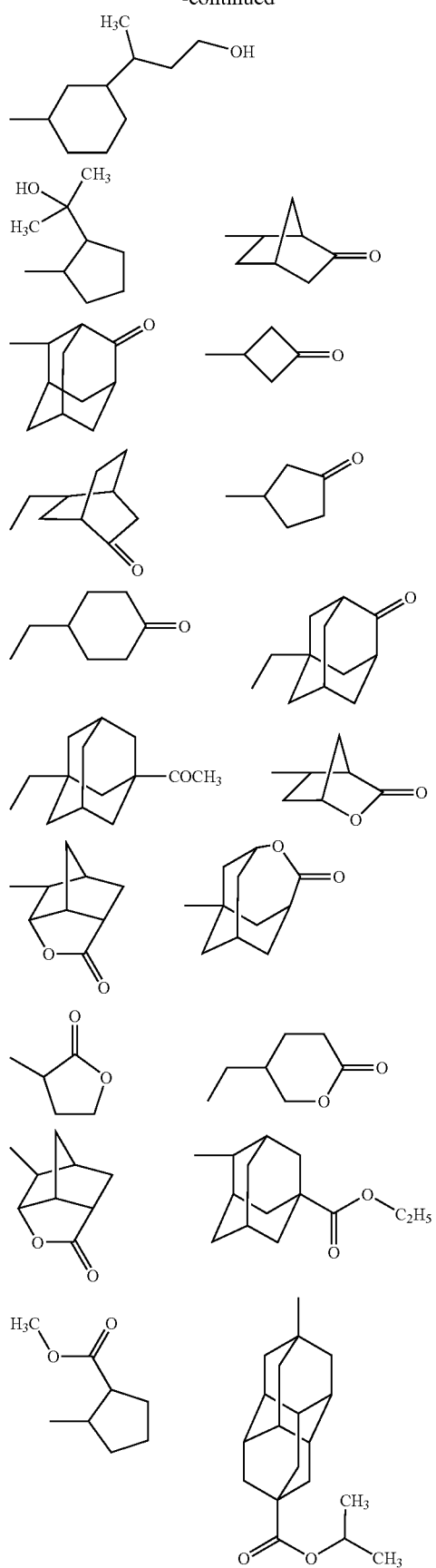
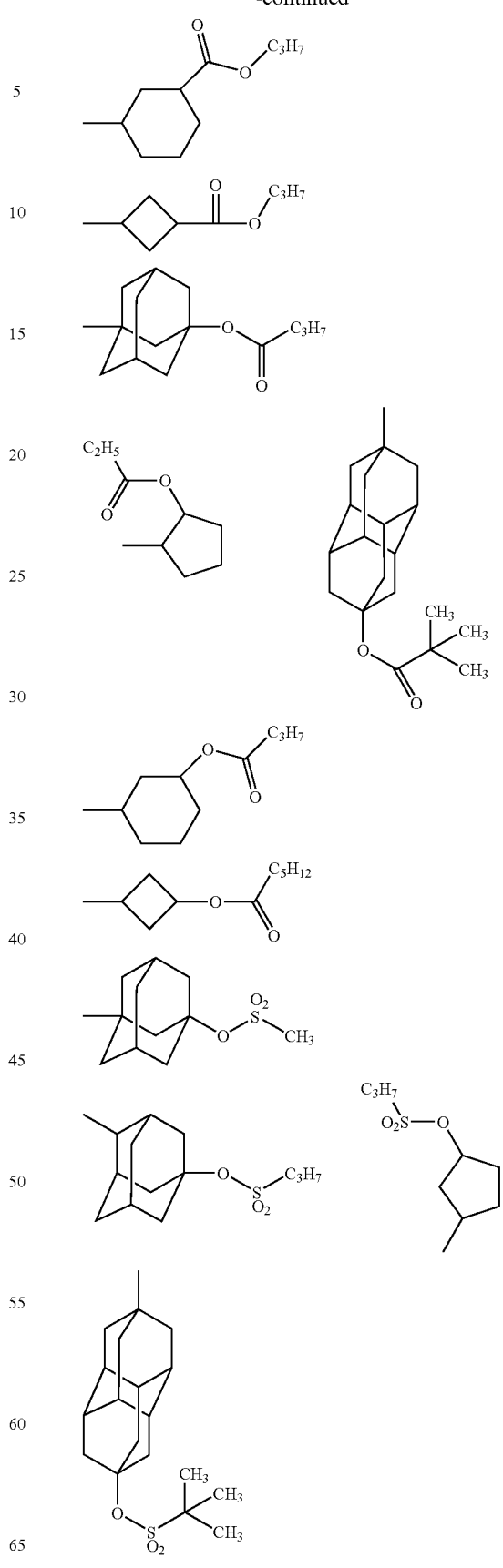

-continued
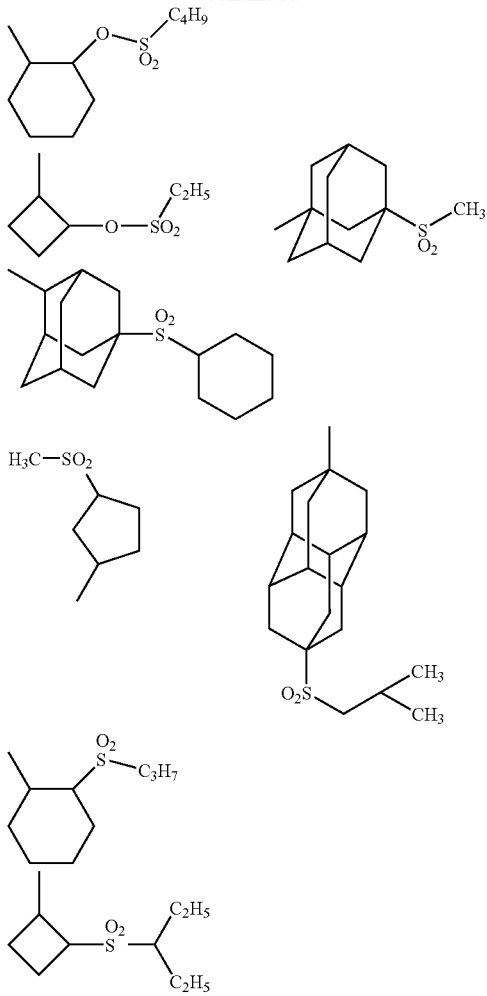
Examples of the C5-C24 aromatic hydrocarbon group include the followings:
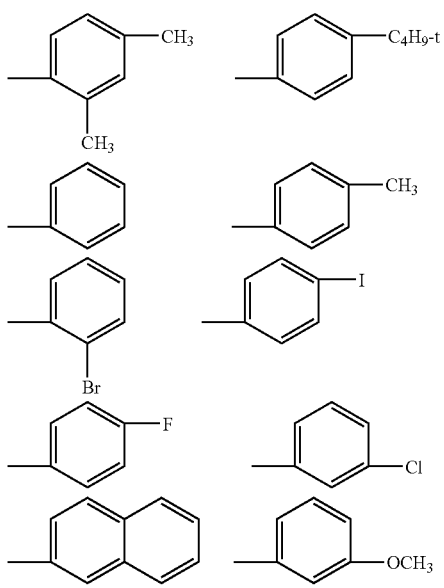
-continued
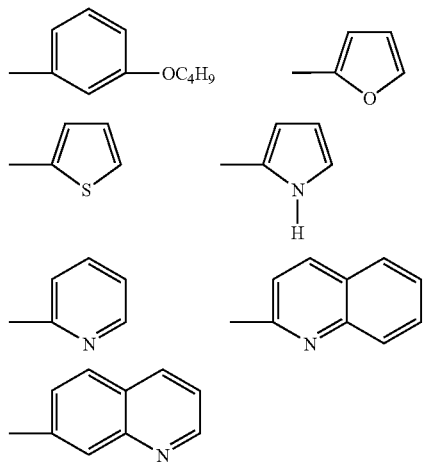
Examples of the C6-C24 aralkyl group include the followings:
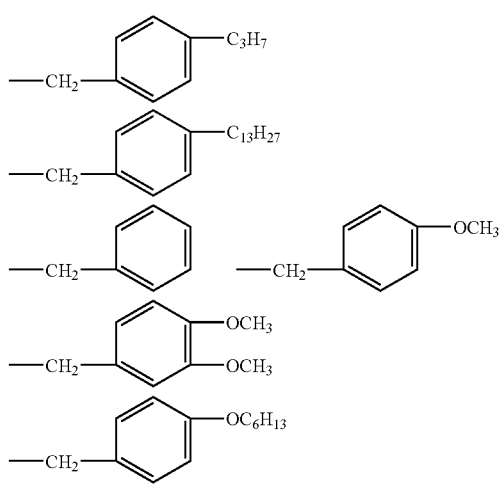

-continued

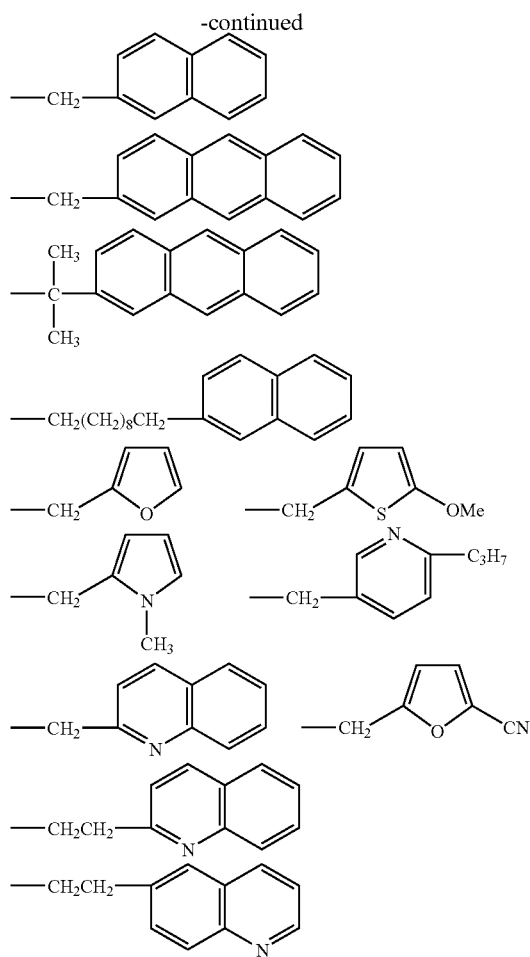

Examples of the group represented by the formula (I-1):

$$-R^2-X^1-R^3 \quad (I\text{-}1)$$

wherein $R^2$ and $R^3$ are the same as defined above, and $X^1$ represents *—CO—CR$^a$R$^b$—CO—O— or *—O—CO—CR$^a$R$^b$—CO— wherein $R^a$ represents a hydrogen atom and $R^b$ and $R^3$ are bonded each other to form a C3-C24 ring, or $R^a$, $R^b$ and $R^3$ are bonded each other to form a C3-C24 ring, and * is a binding site for $R^2$ include a group represented by the formula (Id) and a group represented by the formula (Ie):

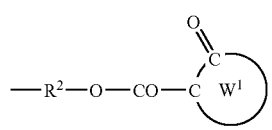
(Id)

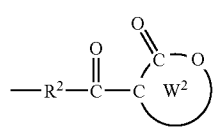
(Ie)

wherein $R^2$ is the same as defined above, $W^1$ represents an optionally substituted C3-C24 hydrocarbon ring group in which one —CH$_2$— is replaced by —CO—, and $W^2$ represents a C3-C24 hydrocarbon ring group in which one —CH$_2$—CH$_2$— is replaced by —CO—O—, and —CH$_2$— in the C3-C24 hydrocarbon ring may be replaced by —NH—, —CO— or —O—. Examples of the substituent include a halogen atom such as a fluorine atom, a hydroxyl group, a cyano group, —OR$^4$—, —CO—OR$^4$, —O—CO—R$^4$, —SO$_2$R$^4$ and —O—SO$_2$—R$^4$ wherein $R^4$ is the same as defined above.

Examples of the hydrocarbon ring group in $W^1$ include the followings:

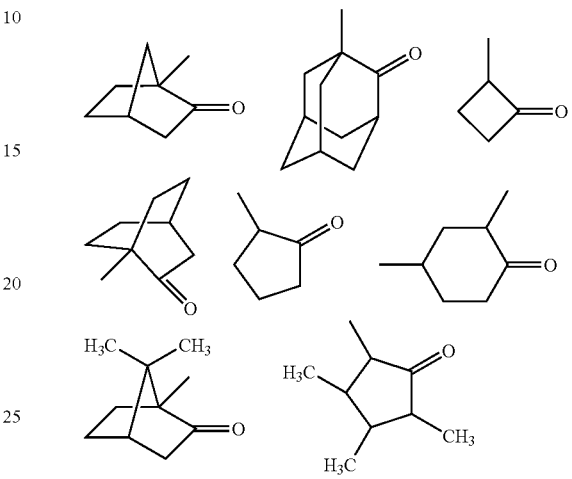

Examples of the hydrocarbon ring in $W^2$ include the followings:

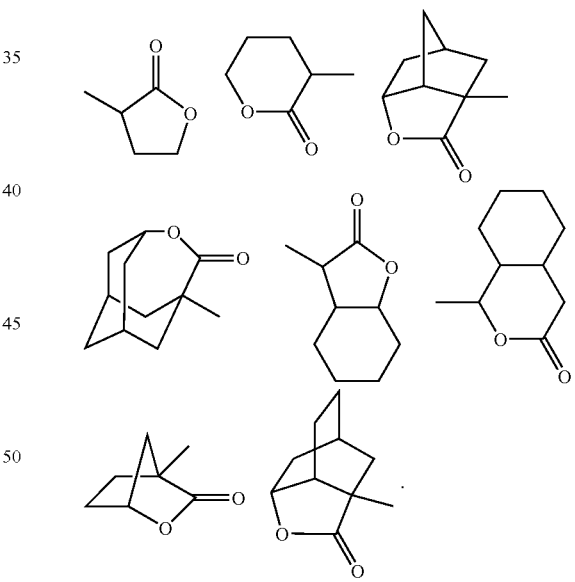

Examples of the sulfonium compound (Ia) include the followings:

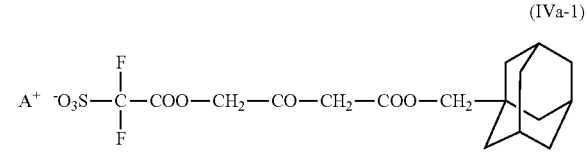
(IVa-1)

-continued (IVb-1)
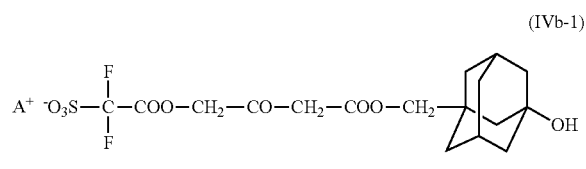

(IVc-1)
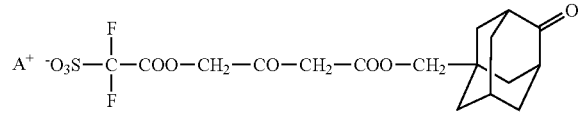

(IVd-1)
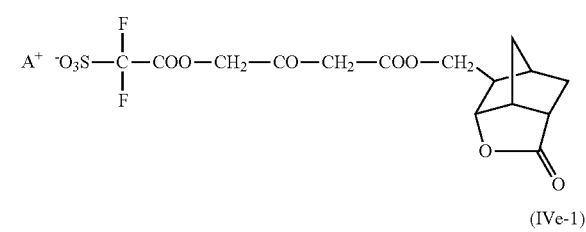

(IVe-1)
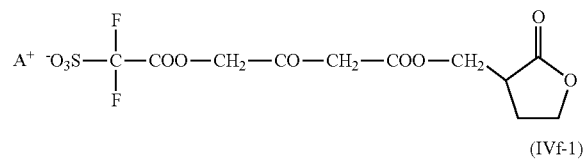

(IVf-1)
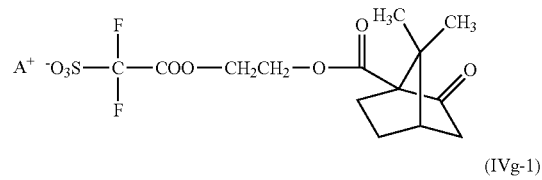

(IVg-1)
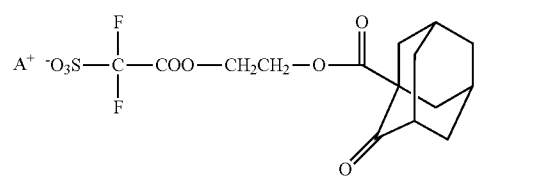

wherein A⁺ is the same as defined above.

Examples of the organic counter ion include cation represented by the formulae (IXz), (IXb), (IXc) and (IXd):

(IXz)
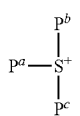

(IXb)
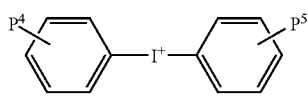

(IXc)
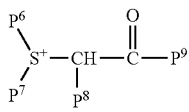

(IXd)
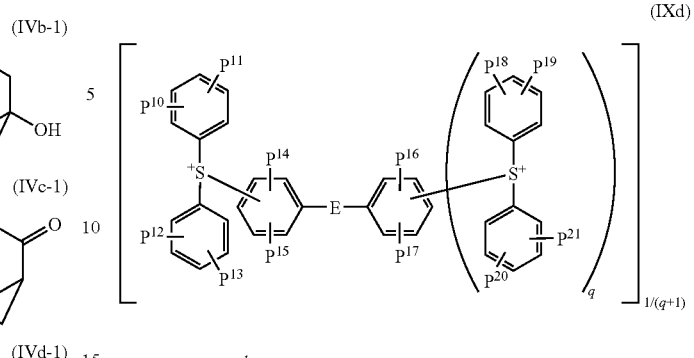

wherein $P^a$, $P^b$ and $P^c$ each independently represent a C1-C30 alkyl group which may have one or more substituents selected from the group consisting of a hydroxyl group, a C3-C12 cyclic hydrocarbon group and a C1-C12 alkoxy group, or a C3-C30 cyclic hydrocarbon group which may have one or more substituents selected from the group consisting of a hydroxyl group and a C1-C12 alkoxy group, $P^4$ and $P^5$ each independently represent a hydrogen atom, a hydroxyl group, a C1-C12 alkyl group or a C1-C12 alkoxy group, $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent S⁺, and one or more —CH₂— in the divalent acyclic hydrocarbon group may be replaced by —CO—, —O— or —S—, $P^8$ represents a hydrogen atom, $P^9$ represents a C1-C12 alkyl group, a C3-C12 cycloalkyl group or a C6-C20 aromatic group which may have one or more substituents, or $P^8$ and $P^9$ are bonded each other to form a divalent acyclic hydrocarbon group which forms a 2-oxocycloalkyl group together with the adjacent —CHCO—, and one or more —CH₂— in the divalent acyclic hydrocarbon group may be replaced by —CO—, —O— or —S—, and $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, E represents a sulfur atom or an oxygen atom and q represents 0 or 1.

Examples of the C1-C12 alkoxy group in the formulae (IXz), (IXb) and (IXd) include a methoxy group, an ethoxy group, a propoxy group, an isopropoxy group, a butoxy group, an isobutoxy group, a sec-butoxy group, a tert-butoxy group, a pentyloxy group, a hexyloxy group, an octyloxy group and a 2-ethylhexyloxy group. Examples of the C3-C12 cyclic hydrocarbon group in the formula (IXz) include a cyclopentyl group, a cyclohexyl group, a 1-adamantyl group, a 2-adamantyl group, a phenyl group, a 2-methylphenyl group, a 4-methylphenyl group, a 1-naphthyl group and a 2-naphthyl group.

Examples of the C1-C30 alkyl group which may have one or more substituents selected from the group consisting of a hydroxyl group, a C3-C12 cyclic hydrocarbon group and a C1-C12 alkoxy group in the formula (IXz) include a methyl group, an ethyl group, a propyl group, an isopropyl group, a butyl group, an isobutyl group, a sec-butyl group, a tert-butyl group, a pentyl group, a hexyl group, an octyl group, a 2-ethylhexyl group and a benzyl group.

Examples of the C3-C30 cyclic hydrocarbon group which may have one or more substituents selected from the group consisting of a hydroxyl group and a C1-C12 alkoxy group in the formula (IXz) include a cyclopentyl group, a cyclohexyl group, a 1-adamantyl group, a 2-adamantyl group, a bicyclohexyl group, a phenyl group, a 2-methylphenyl group, a 4-methylphenyl group, a 4-ethylphenyl group, a 4-isopropylphenyl group, a 4-tert-butylphenyl group, a 2,4-dimethylphenyl group, a 2,4,6-trimethylphenyl group, a 4-hexylphenyl group, a 4-octylphenyl group, a 1-naphthyl group, a 2-naphthyl group, a fluorenyl group, a 4-phenylphenyl group, a 4-hydroxyphenyl group, a 4-methoxyphenyl group, a 4-tert-butoxyphenyl group and a 4-hexyloxyphenyl group.

Examples of the C1-C12 alkyl group in the formulae (IXb), (IXc) and (IXd) include a methyl group, an ethyl group, a propyl group, an isopropyl group, a butyl group, an isobutyl group, a sec-butyl group, a tert-butyl group, a pentyl group, a hexyl group, an octyl group and a 2-ethylhexyl group.

Examples of the C3-C12 cycloalkyl group in the formula (IXc) include a cyclopropyl group, a cyclobutyl group, a cyclopentyl group, a cyclohexyl group, a cycloheptyl group, a cyclooctyl group and a cyclodecyl group. Examples of the C3-C12 divalent acyclic hydrocarbon group formed by bonding $P^6$ and $P^7$ include a trimethylene group, a tetramethylene group and a pentamethylene group. Examples of the ring group formed together with the adjacent $S^+$ and the divalent acyclic hydrocarbon group include a tetramethylenesulfonio group, a pentamethylenesulfonio group and an oxybisethylenesulfonio group.

Examples of the C6-C20 aromatic group which may have one or more substituents in the formula (IXc) include a phenyl group, a tolyl group, a xylyl group, a tert-butylphenyl group and a naphthyl group. Examples of the divalent acyclic hydrocarbon group formed by bonding $P^8$ and $P^9$ include a methylene group, an ethylene group, a trimethylene group, a tetramethylene group and a pentamethylene group and examples of the 2-oxocycloalkyl group formed together with the adjacent —CHCO— and the divalent acyclic hydrocarbon group include a 2-oxocyclopentyl group and a 2-oxocyclohexyl group.

The cation represented by the formula (IXz) is preferable and a cation represented by the formula (IIIa):

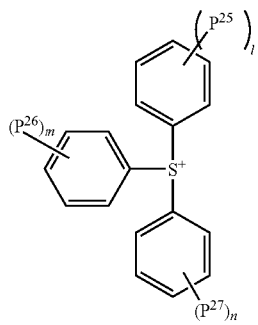

(IIIa)

wherein $P^{25}$, $P^{26}$ and $P^{27}$ are independently in each occurrence a hydroxyl group, a halogen atom, a C1-C12 alkyl group, a C1-C12 alkoxy group or a C3-C12 cyclic hydrocarbon group, and the C3-C12 cyclic hydrocarbon group may have a halogen atom, a hydroxyl group or a C1-C12 alkoxy group, and l, m and n each independently represent an integer of 0 to 5, is more preferable.

In the formula (IIIa), examples of the halogen atom include a fluorine atom, a chlorine atom, a bromine atom and an iodine atom, and a fluorine atom, a chlorine atom and a bromine atom are preferable, and a fluorine atom is more preferable. Examples of the C1-C12 alkyl group include a methyl group, an ethyl group, a propyl group, an isopropyl group, a butyl group, an isobutyl group, a sec-butyl group, a tert-butyl group, a pentyl group, a hexyl group, an octyl group and a 2-ethylhexyl group. Examples of the C1-C12 alkoxy group include a methoxy group, an ethoxy group, a propoxy group, a butoxy group, a hexyloxy group, an octyloxy group and a 2-ethylhexyloxy group. Examples of the C3-C12 cyclic hydrocarbon group, and the C3-C12 cyclic hydrocarbon group may have a halogen atom, a hydroxyl group or a C1-C12 alkoxy group include a group having an adamantyl skeleton and a group having an isobornyl skeleton, and preferable examples thereof include a 2-alkyl-2-adamantyl group, a 1-(1-adamantyl)-1-alkyl group and an isobornyl group.

Examples of the cation represented by the formula (IIIa) include the followings.

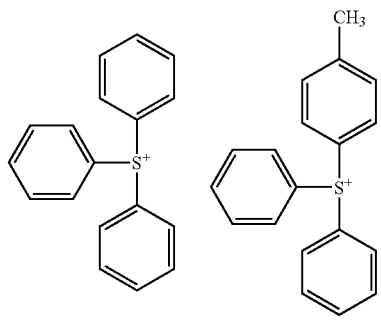

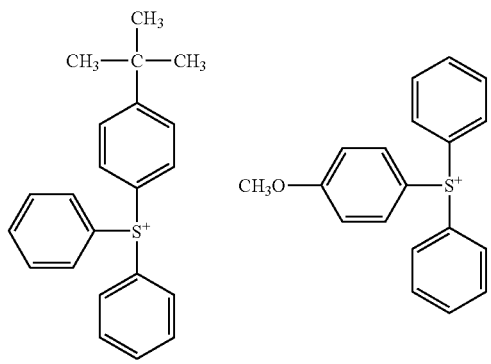

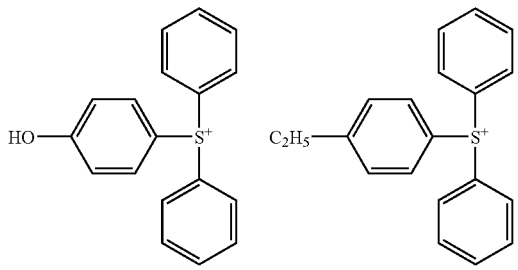

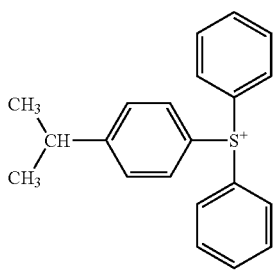

-continued
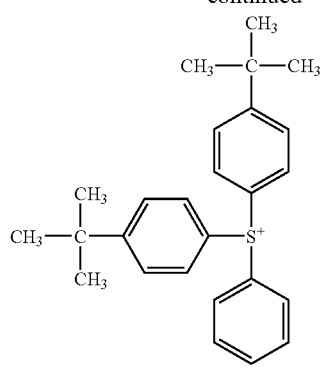
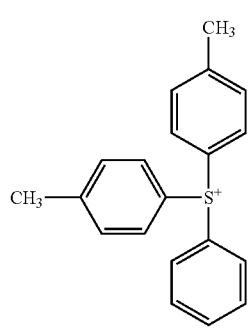
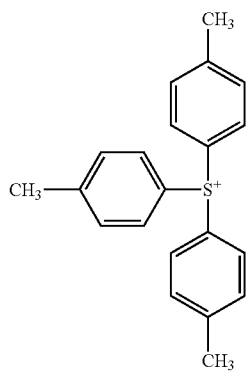
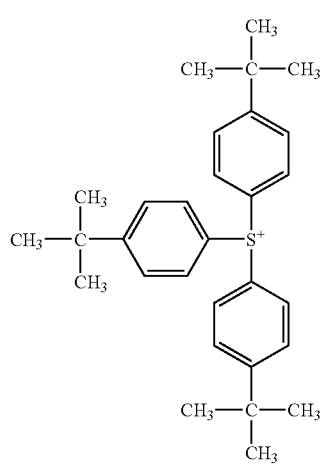
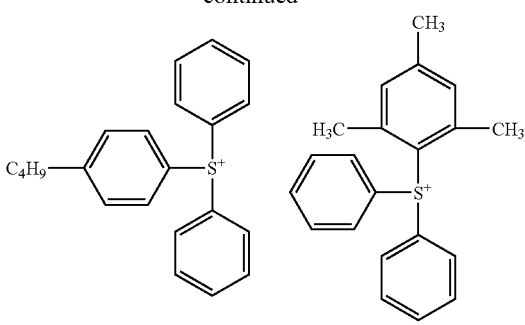
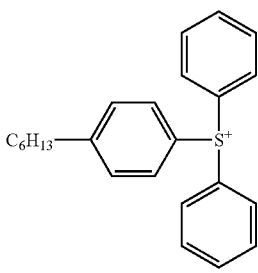
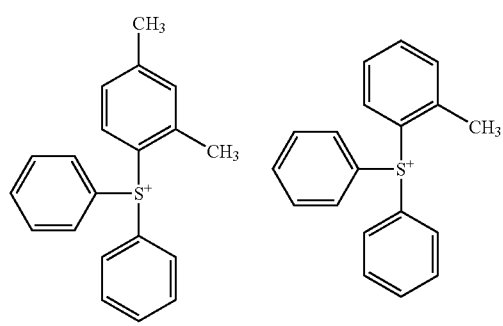
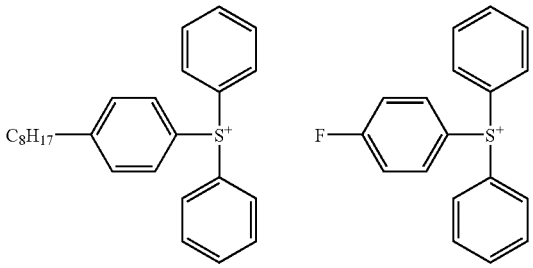
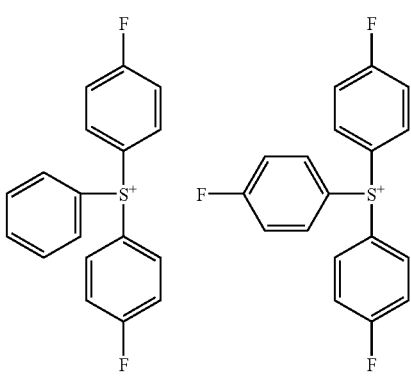

Among the cations represented by the formula (IIIa), a cation represented by the formula (IXe):

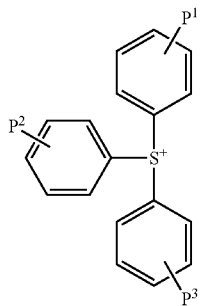

(IXe)

wherein $P^1$, $P^2$ and $P^3$ each independently represent a hydrogen atom, a hydroxyl group, a halogen atom, a C1-C12 alkyl group or a C1-C12 alkoxy group, is more preferable since they can be easily produced.

Examples of the cation represented by the formula (IXb) include the followings.

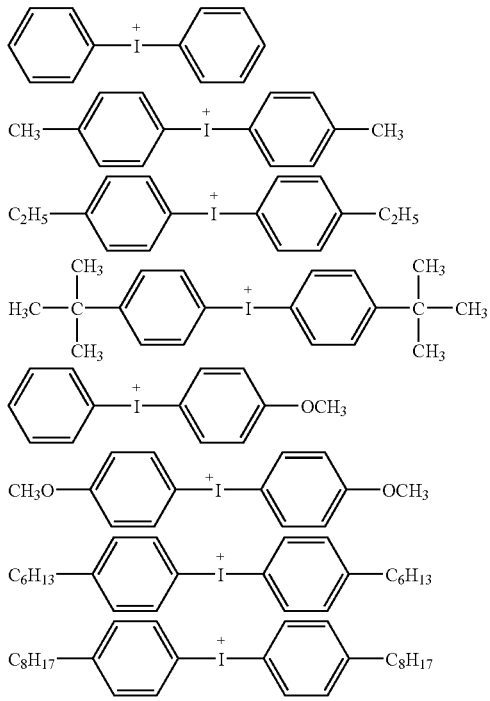

Examples of the cation represented by the formula (IXc) include the followings.

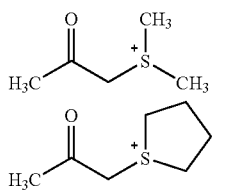

-continued

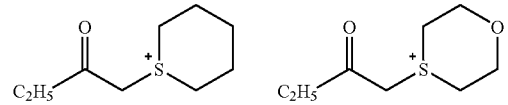

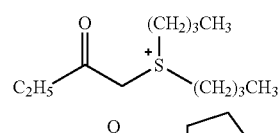

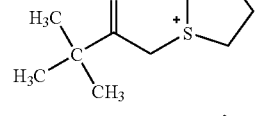

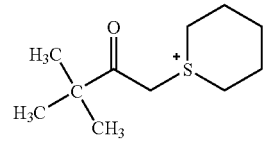

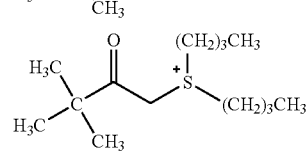

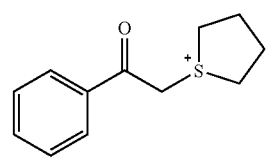

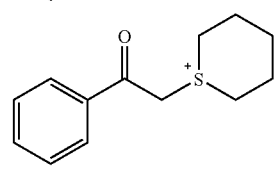

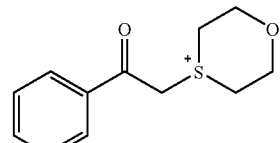

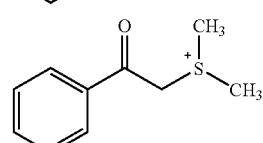

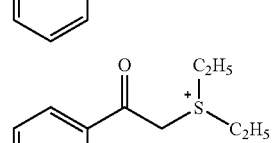

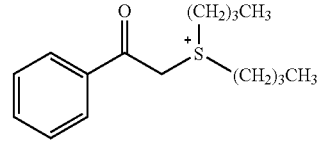

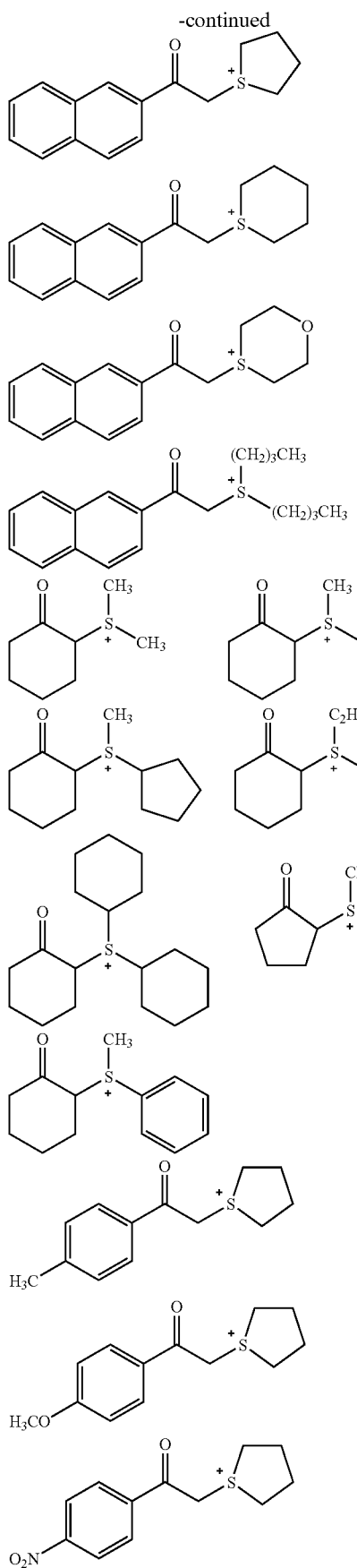
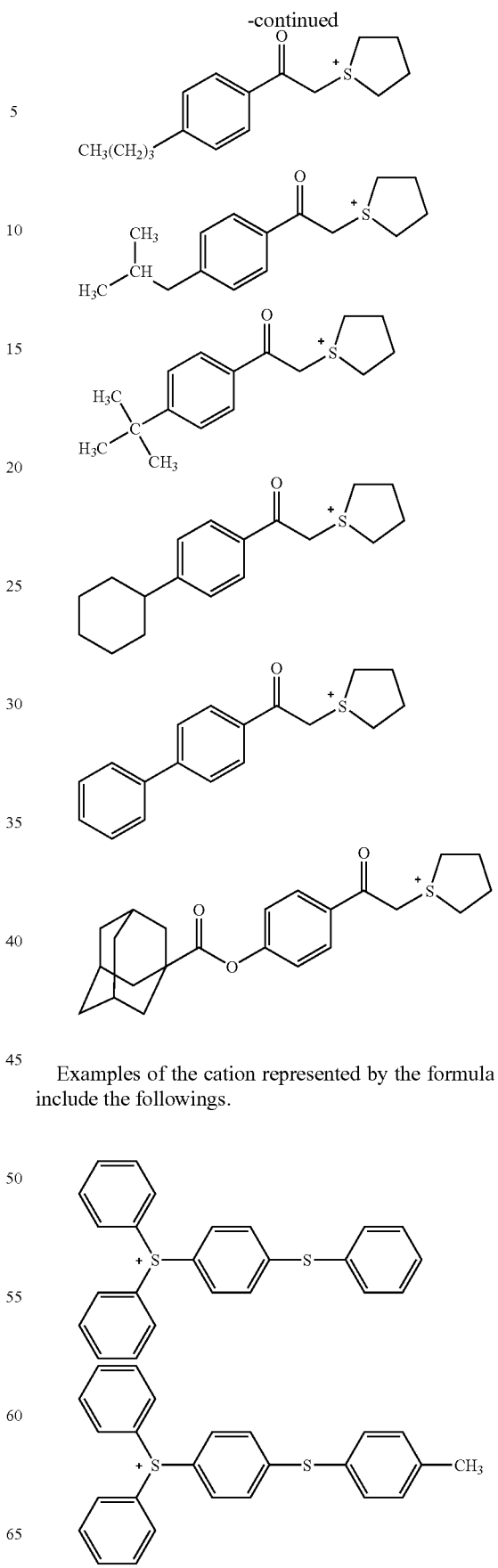
Examples of the cation represented by the formula (IXd) include the followings.
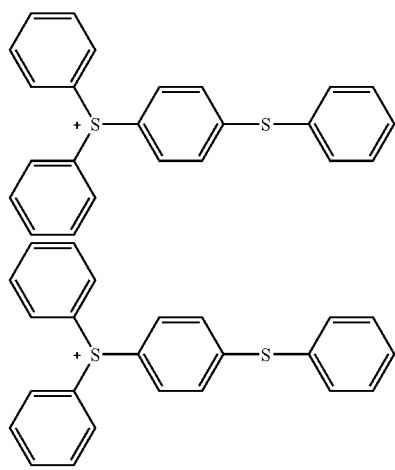

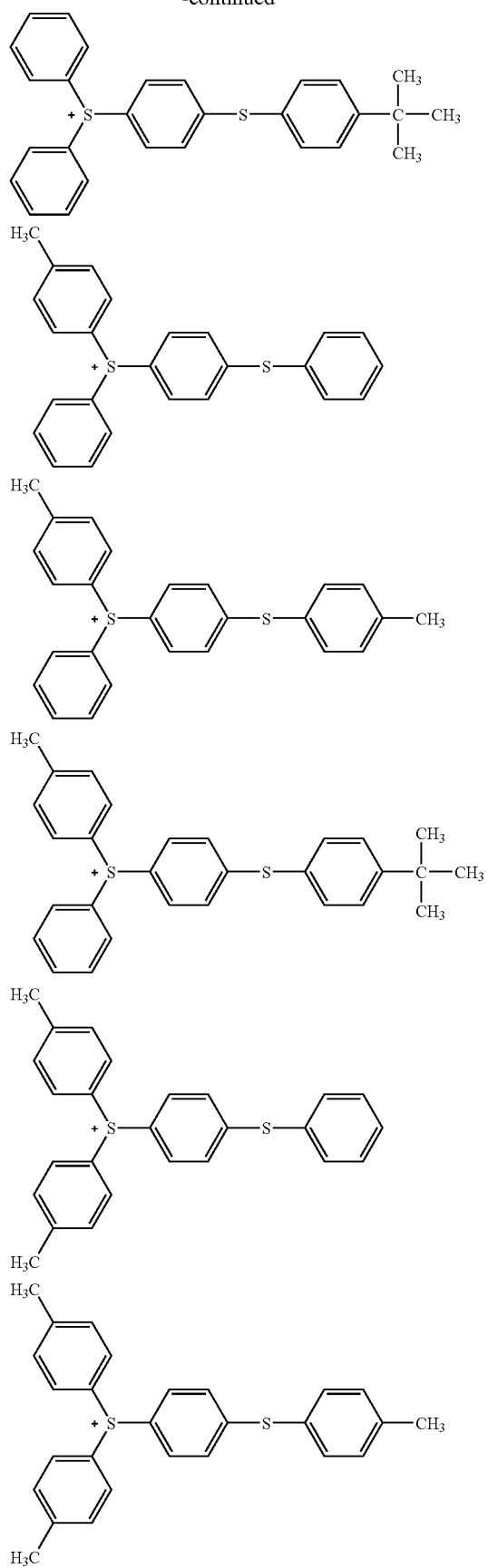
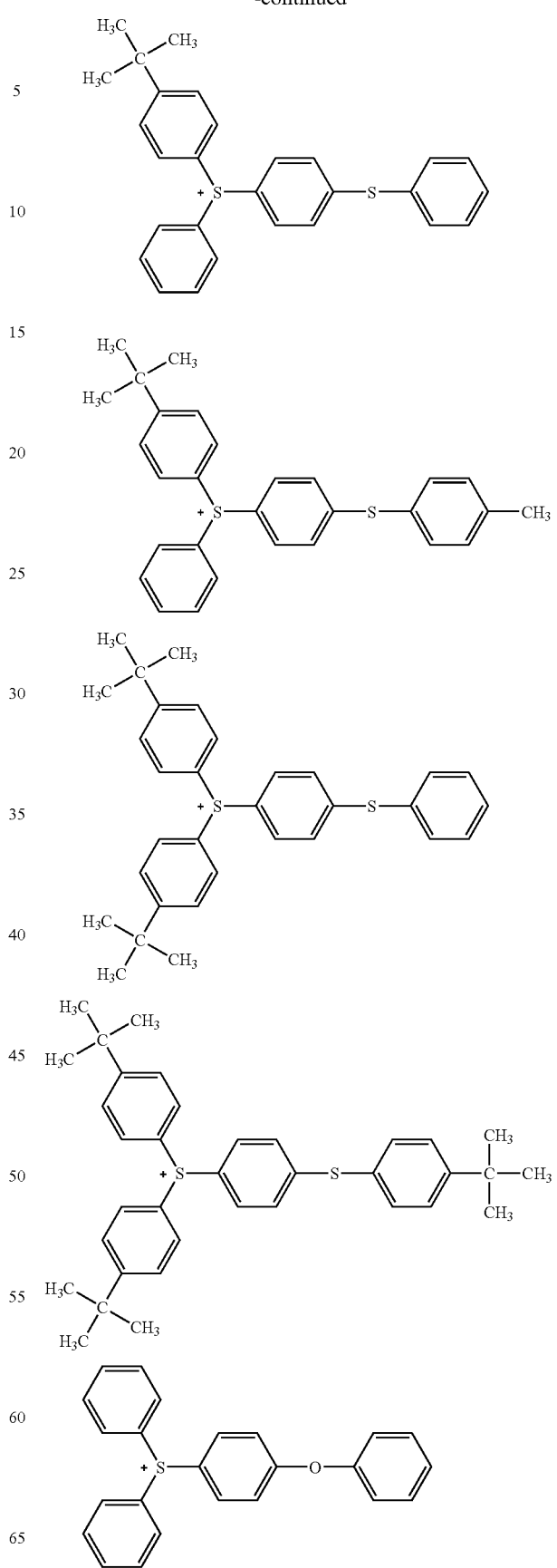

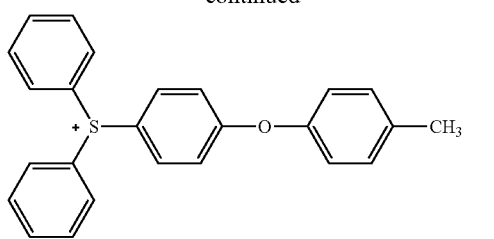
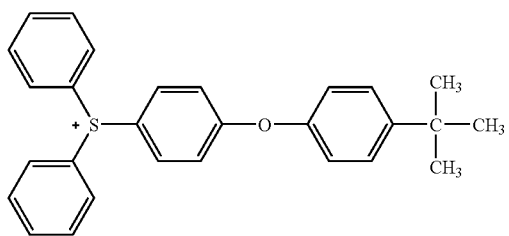
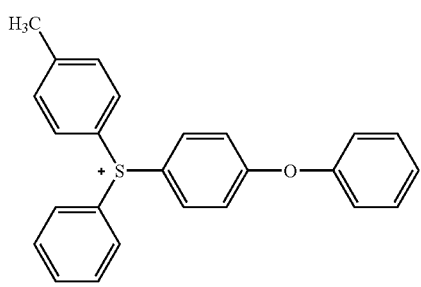
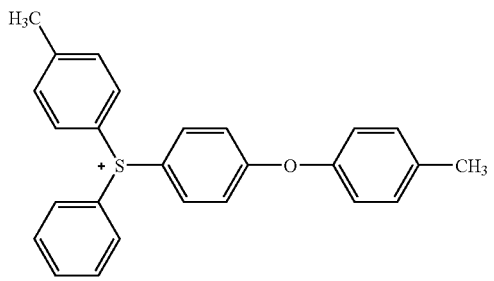
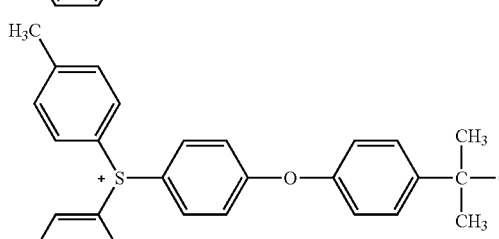
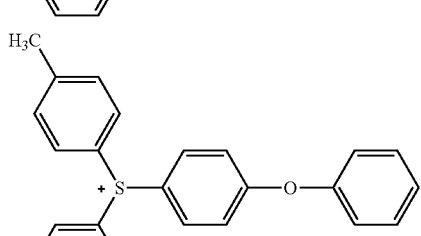
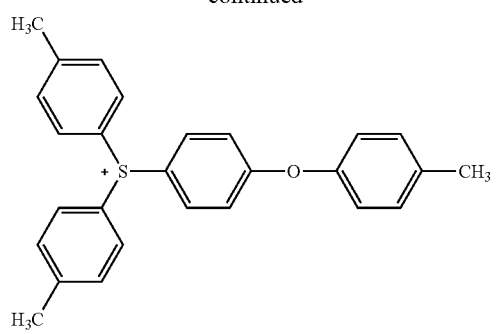
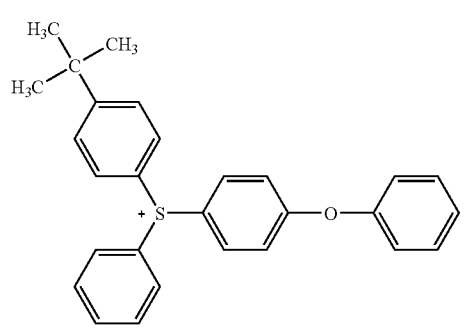
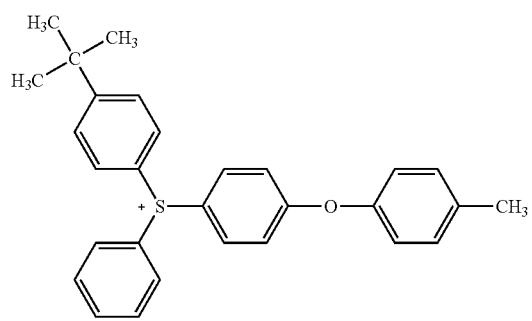
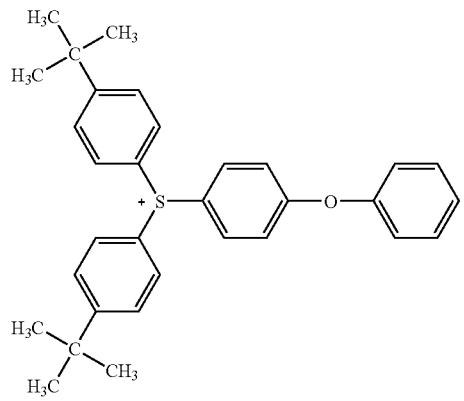

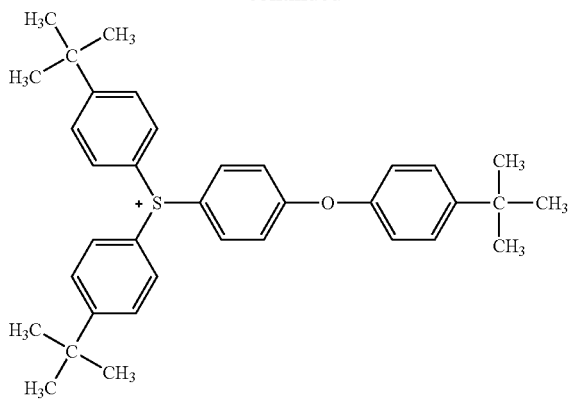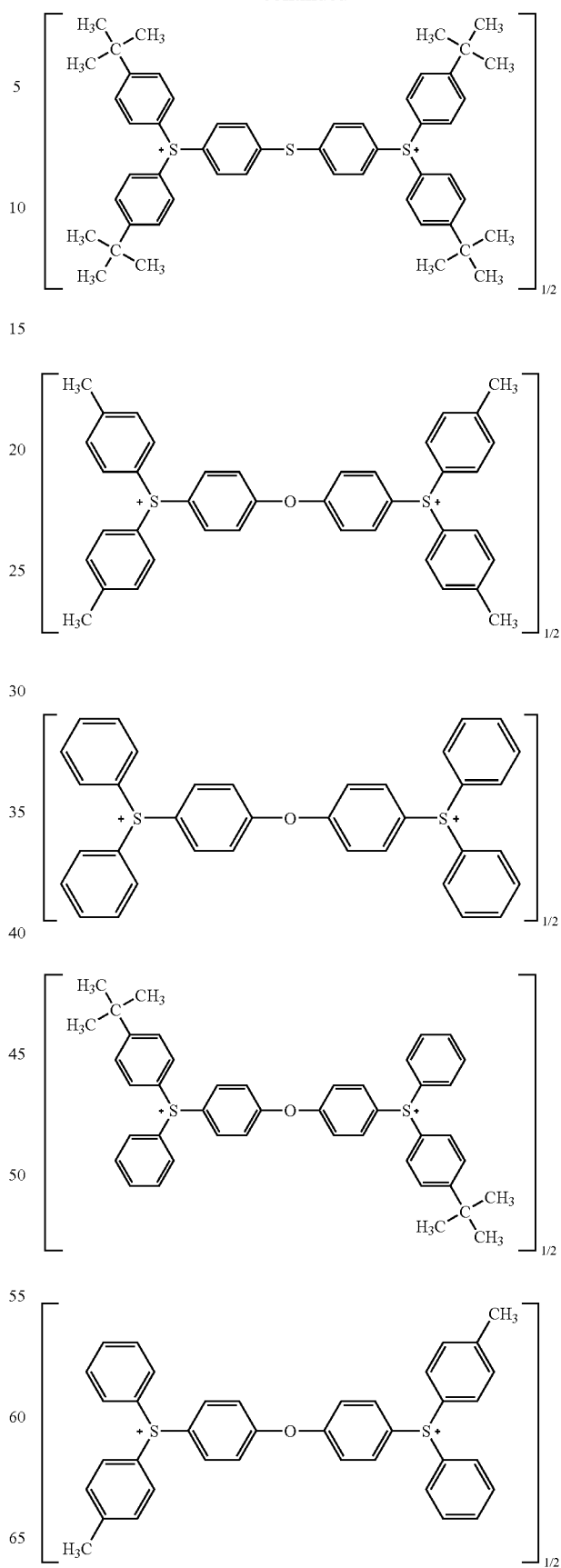

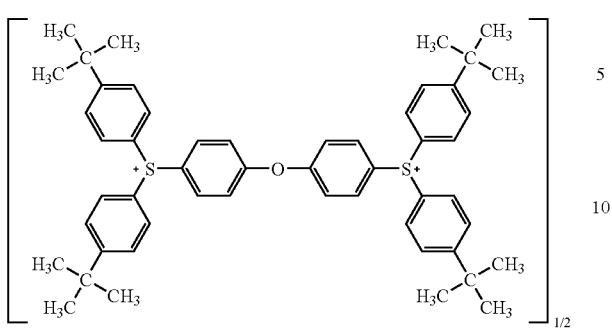

As the sulfonium compound (Ia), a sulfonium compound represented by the formula (IVa-2), a sulfonium compound represented by the formula (IVb-2), a sulfonium compound represented by the formula (IVc-2), a sulfonium compound represented by the formula (IVd-2), a sulfonium compound represented by the formula (IVe-2), a sulfonium compound represented by the formula (IVf-2) and a sulfonium compound represented by the formula (IVg-2):

(IVa-2)

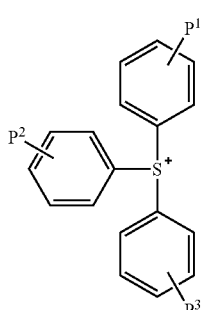

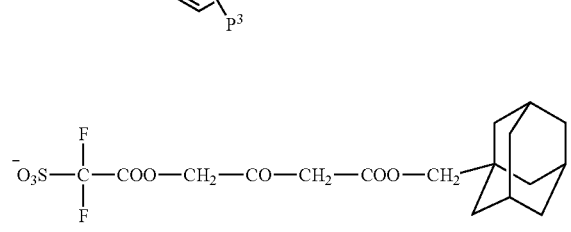

(IVb-2)

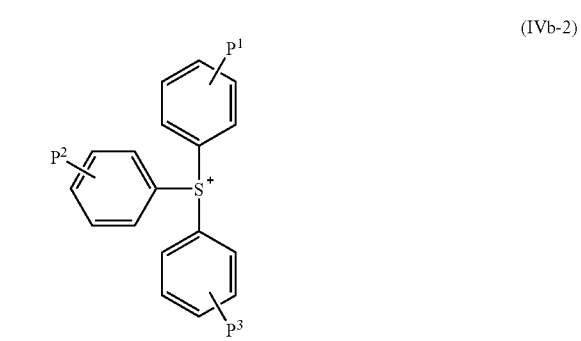

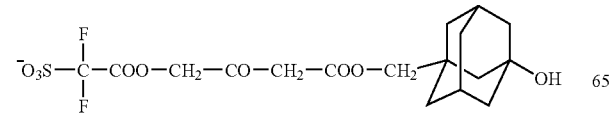

(IVc-2)

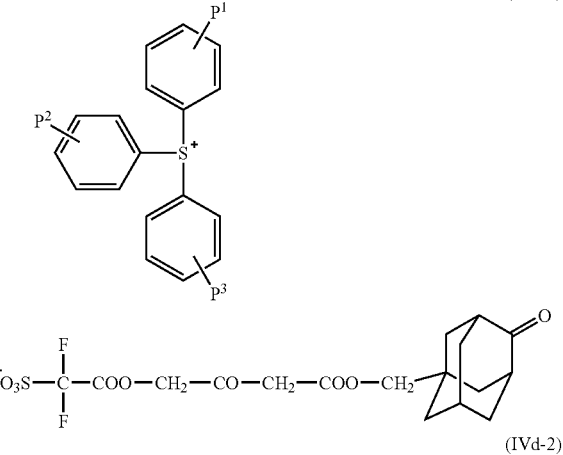

(IVd-2)

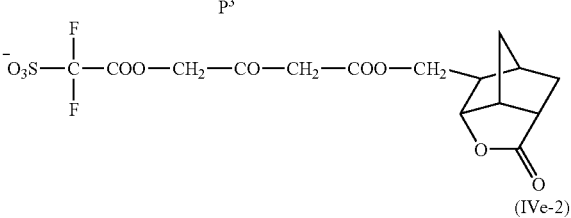

(IVe-2)

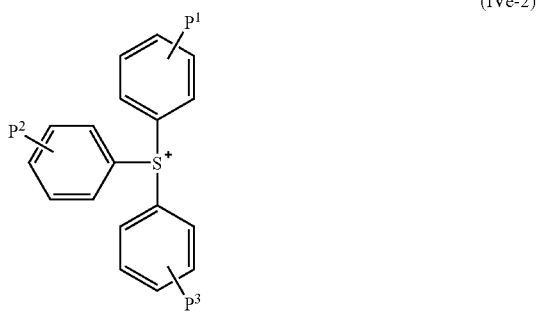

(IVf-2)

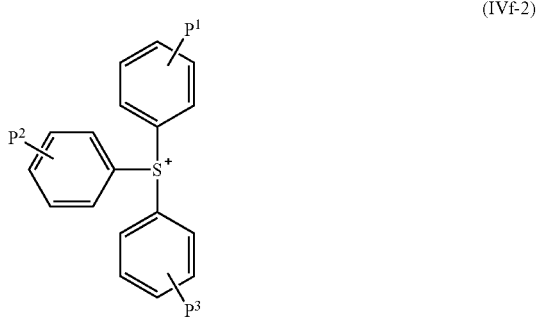

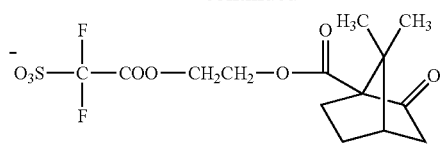
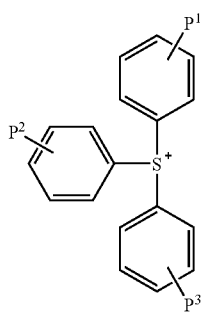
(IVg-2)
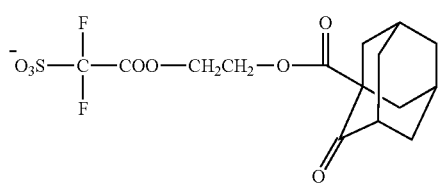
wherein P¹, P² and P³ are the same as defined above, are preferable, and sulfonium compounds represented by the following formulae are more preferable.
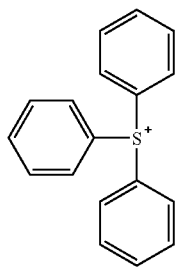
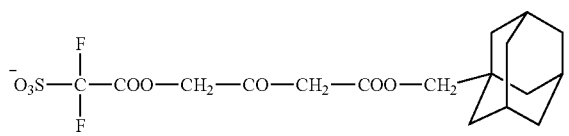
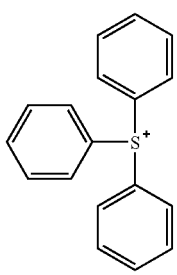
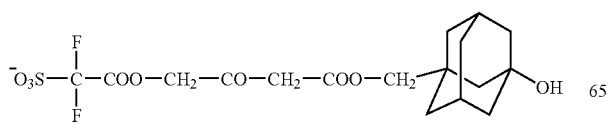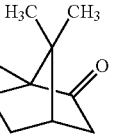
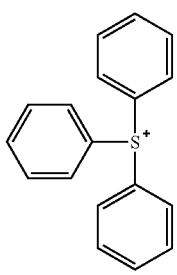
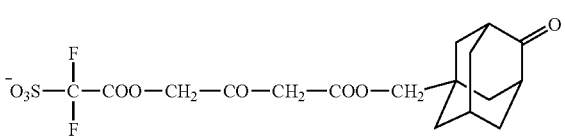
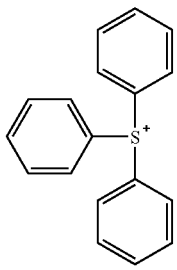
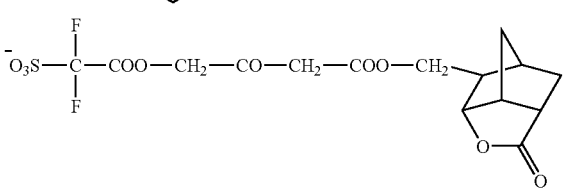
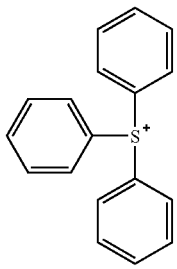

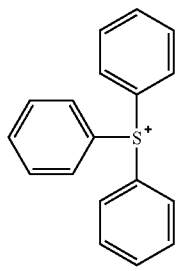

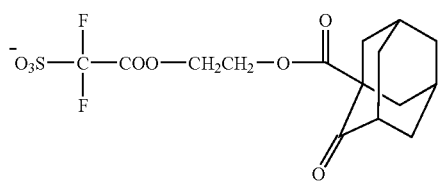

The sulfonium compound (Ia) can be produced by a process comprising reacting a compound represented by the formula (VI):

$$Z—R^1 \quad (VI)$$

wherein $R^1$ is the same as defined above, and Z represents a halogen atom, with a salt represented by the formula (VII):

(VII)

wherein $Q^1$, $Q^2$ and $A^+$ are the same as defined above.

The amount of the compound represented by the formula (VI) to be used is usually 0.9 to 3 moles and preferably 1 to 2 moles per 1 mole of the salt represented by the formula (VII). The reaction of the compound represented by the formula (VI) and the salt (VII) is usually conducted in an inert solvent such as water, acetonitrile, chloroform and dichloromethane, at a temperature of 0 to 100° C., preferably of 0 to 60° C. The reaction is usually carried out in the presence of a base, and examples of the base include an inorganic base such as sodium hydroxide, potassium hydroxide and potassium carbonate, and an organic base such as pyridine, lutidine and triethylamine. The amount of the base to be used is usually 1 to 3moles and preferably 1 to 2 moles per 1 mole of the salt represented by the formula (VII). The sulfonium compound (Ia) obtained may be taken out by crystallization or washing with water.

Alternatively, the sulfonium compound (Ia) can be also produced by a process comprising reacting a compound represented by the formula (VIII):

$$A^+L^- \quad (VIII)$$

wherein $A^+$ is the same as defined above, and $L^-$ represents $F^-$, $Cl^-$, $Br^-$, $I^-$, $BF_4^-$, $AsF_6^-$, $SbF_6^-$, $PF_6^-$ or $ClO_4^-$, with a salt represented by the formula (IX):

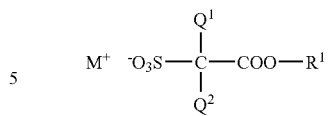

(IX)

wherein $Q^1$, $Q^2$ and $R^1$ are the same as defined above and $M^+$ is $Li^+$, $Na^+$ or W. The amount of the compound represented by the formula (VIII) to be used is usually 0.9 to 2 moles and preferably 1 to 1.5 moles per 1 mole of the salt represented by the formula (IX).

The chemically amplified photoresist composition comprises the sulfonium compound (Ia) and a resin comprising a structural unit having an acid-labile group and being insoluble or poorly soluble in an aqueous alkali solution but becoming soluble in an aqueous alkali solution by the action of an acid.

The photoresist composition may two or more kinds of the sulfonium compound (Ia). The photoresist composition may two or more kinds of the resins.

The sulfonium compound (Ia) works as an acid generator in the photoresist composition. The photoresist composition also may contain the other acid generator(s).

The acid generator is a substance which is decomposed to generate an acid by applying a radiation such as a light, an electron beam or the like on the substance itself or on a photoresist composition containing the substance. The acid generated from the acid generator acts on the resin resulting in cleavage of the acid-labile group existing in the resin, and the resin becomes soluble in an aqueous alkali solution.

In this specification, "an acid-labile group" means a group capable of being eliminated by the action of an acid.

In this specification, "—COOR" may be described as "a structure having ester of carboxylic acid", and may also be abbreviated as "ester group". Specifically, "—COOC(CH$_3$)$_3$" may be described as "a structure having tert-butyl ester of carboxylic acid", or be abbreviated as "tert-butyl ester group".

Examples of the acid-labile group include a structure having ester of carboxylic acid such as alkyl ester group in which a carbon atom adjacent to the oxygen atom is quaternary carbon atom, alicyclic ester group in which a carbon atom adjacent to the oxygen atom is quaternary carbon atom, and a lactone ester group in which a carbon atom adjacent to the oxygen atom is quaternary carbon atom.

The "quaternary carbon atom" means a "carbon atom joined to four substituents other than hydrogen atom". Other examples of the acid-labile group include a group having a quaternary carbon atom joined to three carbon atoms and an —OR', wherein R' represents an alkyl group.

Examples of the acid-labile group include an alkyl ester group in which a carbon atom adjacent to the oxygen atom is quaternary carbon atom such as a tert-butyl ester group; an acetal type ester group such as a methoxymethyl ester, ethoxymethyl ester, 1-ethoxyethyl ester, 1-isobutoxyethyl ester, 1-isopropoxyethyl ester, 1-ethoxypropoxy ester, 1-(2-methoxyethoxy)ethyl ester, 1-(2-acetoxyethoxy)ethyl ester, 1-[2-(1-adamantyloxy)ethoxy]ethyl ester, 1-[2-(1-adamantanecarbonyloxy)ethoxy]ethyl ester, tetrahydro-2-furyl ester and tetrahydro-2-pyranyl ester group; an alicyclic ester group in which a carbon atom adjacent to the oxygen atom is quaternary carbon atom, such as an isobornyl ester, 1-alkylcycloalkyl ester, 2-alkyl-2-adamantyl ester and 1-(1-adamantyl)-1-alkylalkyl ester group. The above-mentioned adamantyl group may have one or more hydroxyl groups.

Examples of the structural unit having an acid-labile group include a structure unit derived from an ester of acrylic acid, a structural unit derived from an ester of methacrylic acid, a structural unit derived from an ester of norbornenecarboxylic acid, a structural unit derived from an ester of tricyclodecenecarboxylic acid and a structural unit derived from an ester of tetracyclodecenecarboxylic acid. The structure units derived from the ester of acrylic acid and from the ester of methacrylic acid are preferable.

The resin can be obtained by conducting polymerization reaction of a monomer or monomers having the acid-labile group and an olefinic double bond. The polymerization reaction is usually carried out in the presence of a radical initiator.

Among the monomers, those having a bulky and acid-labile group such as an alicyclic ester group (e.g. a 1-alkyl-1-cyclohexyl ester group, a 2-alkyl-2-adamantyl ester and 1-(1-adamantyl)-1-alkylalkyl ester group) are preferable, since excellent resolution is obtained when the resin obtained is used in the photoresist composition.

Examples of such monomer containing the bulky and acid-labile group include a 1-alkyl-1-cyclohexyl acrylate, a 1-alkyl-1-cyclohexylmethacrylate, a 2-alkyl-2-adamantyl acrylate, a 2-alkyl-2-adamantyl methacrylate, 1-(1-adamantyl)-1-alkylalkyl acrylate, a 1-(1-adamantyl)-1-alkylalkyl methacrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate and a 1-(1-adamantyl)-1-alkylalkyl α-chloroacrylate.

Particularly when the 2-alkyl-2-adamantyl acrylate, the 2-alkyl-2-adamantyl methacrylate or the 2-alkyl-2-adamantyl α-chloroacrylate is used as the monomer for the resin component in the photoresist composition, a photoresist composition having excellent resolution tend to be obtained. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantyl acrylate, 2-methyl-2-adamantyl α-chloroacrylate and 2-ethyl-2-adamantyl α-chloroacrylate.

When particularly 2-ethyl-2-adamantyl acrylate, 2-ethyl-2-adamantyl methacrylate, 2-isopropyl-2-adamantyl acrylate or 2-isopropyl-2-adamantyl methacrylate is used for the photoresist composition, a photoresist composition having excellent sensitivity and heat resistance tends to be obtained. Two or more kinds of monomers having a group or groups dissociated by the action of the acid may be used together, if necessary.

The 2-alkyl-2-adamantyl acrylate can be usually produced by reacting a 2-alkyl-2-adamantanol or a metal salt thereof with an acrylic halide, and the 2-alkyl-2-adamantyl methacrylate can be usually produced by reacting a 2-alkyl-2-adamantanol or a metal salt thereof with a methacrylic halide.

Examples of the 1-alkyl-1-cyclohexyl acrylate include 1-ethyl-1-cyclohexyl acrylate, and examples of the 1-alkyl-1-cyclohexyl methacrylate include 1-ethyl-1-cyclohexyl methacrylate.

The resin used for the photoresist composition can also contain other structural unit or units derived from an acid-stable monomer in addition to the above-mentioned structural units having the acid-labile group. Herein, the "structural unit derived from an acid-stable monomer" means "a structural unit not dissociated by an acid.

Examples of such other structural unit derived from the acid-stable monomer include a structural unit derived from a monomer having a free carboxyl group such as acrylic acid and methacrylic acid; a structural unit derived from an aliphatic unsaturated dicarboxylic anhydride such as maleic anhydride and itaconic anhydride; a structural unit derived from 2-norbornene; a structural unit derived from acrylonitrile or methacrylonitrile; a structural unit derived from an alkyl acrylate or an alkyl methacrylate in which a carbon atom adjacent to oxygen atom is secondary or tertiary carbon atom; a structural unit derived from 1-adamantyl acrylate or 1-adamantyl methacrylate; a structural unit derived from styrene monomer such as p-hydroxystyrene and m-hydroxystyrene; a structural unit derived from acryloyloxy-γ-butyrolactone or methacryloyloxy-γ-butyrolactone having a lactone ring which may have an alkyl group; and the like. Herein, the 1-adamantyloxycarbonyl group is the acid-stable group though the carbon atom adjacent to oxygen atom is the quaternary carbon atom, and the 1-adamantyloxycarbonyl group may have one or more hydroxyl groups.

Specific examples of the structural unit derived from the acid-stable monomer include a structural unit derived from 3-hydroxy-1-adamantyl acrylate;

a structural unit derived from 3-hydroxy-1-adamantyl methacrylate;

a structural unit derived from 3,5-dihydroxy-1-adamantyl acrylate;

a structural unit derived from 3,5-dihydroxy-1-adamantyl methacrylate;

a structural unit derived from α-acryloyloxy-γ-butyrolactone;

a structural unit derived from α-methacryloyloxy-γ-butyrolactone;

a structural unit derived from β-acryloyloxy-γ-butyrolactone;

a structural unit derived from β-methacryloyloxy-γ-butyrolactone;

a structural unit represented by the formula (a):

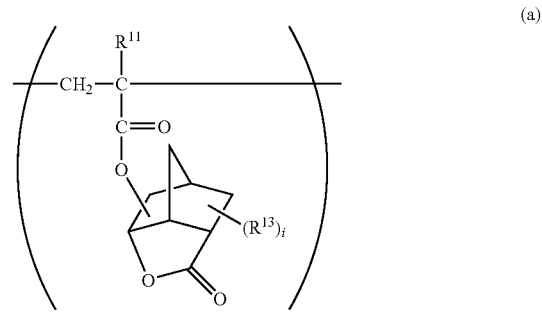

(a)

wherein $R^{11}$ represents a hydrogen atom or a methyl group, $R^{13}$ is independently in each occurrence a methyl group, a trifluoromethyl group or a halogen atom, and i represents an integer of 0 to 3; a structural unit represented by the formula (b):

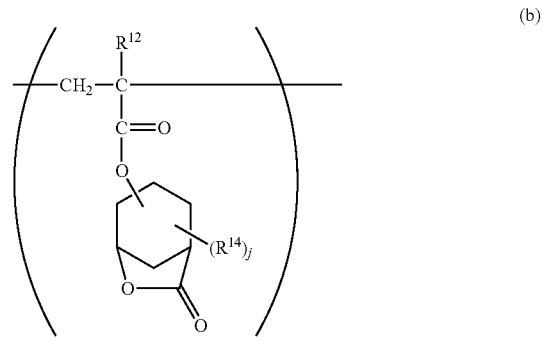

(b)

wherein $R^{12}$ represents a hydrogen atom or a methyl group, $R^{14}$ is independently in each occurrence a methyl group, a trifluoromethyl group or a halogen atom, and j represents an integer of 0 to 3;
a structural unit derived from p-hydroxystyrene;
a structural unit derived from m-hydroxystyrene;
a structural unit derived from an alicyclic compound having an olefinic double bond such as a structural unit represented by the formula (c):

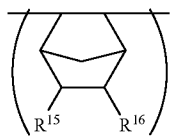
(c)

wherein $R^{15}$ and $R^{16}$ each independently represents a hydrogen atom, a C1-C3 alkyl group, a C1-C3 hydroxyalkyl group, a carboxyl group, a cyano group, a hydroxyl group or a —COOU group in which U represents an alcohol residue, or $R^{15}$ and $R^{16}$ can be bonded together to form a carboxylic anhydride residue represented by —C(=O)OC(=O)—;
a structural unit derived from an aliphatic unsaturated dicarboxylic anhydride such as a structural unit represented by the formula (d):

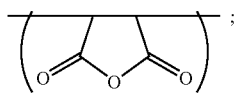
(d)

a structural unit represented by the formula (e):

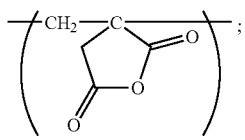
(e)

and the like.

Particularly, the resin having further at least one structural unit selected from the group consisting of the structural unit derived from p-hydroxystyrene, the structural unit derived from m-hydroxystyrene, the structural unit derived from 3-hydroxy-1-adamantyl acrylate, the structural unit derived from 3-hydroxy-1-adamantyl methacrylate, the structural unit derived from 3,5-dihydroxy-1-adamantyl acrylate, the structural unit derived from 3,5-dihydroxy-1-adamantyl methacrylate, the structural unit represented by the formula (a) and the structural unit represented by the formula (b) in addition to the structural unit having the acid-labile group is preferable from the standpoint of the adhesiveness of resist to a substrate and resolution of resist.

3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting corresponding hydroxyadamantane with acrylic acid, methacrylic acid or its acid halide, and they are also commercially available.

Further, the acryloyloxy-γ-butyrolactone and the methacryloyloxy-γ-butyrolactone can be produced by reacting corresponding α- or β-bromo-γ-butyrolactone with acrylic acid or methacrylic acid, or reacting corresponding α- or β-hydroxy-γ-butyrolactone with the acrylic halide or the methacrylic halide.

Examples of the monomers to give structural units represented by the formulae (a) and (b) include an acrylate of alicyclic lactones and a methacrylate of alicyclic lactones having the hydroxyl group described below, and mixtures thereof. These esters can be produced, for example, by reacting the corresponding alicyclic lactone having the hydroxyl group with acrylic acid or methacrylic acid, and the production method thereof is described in, for example, JP 2000-26446 A.

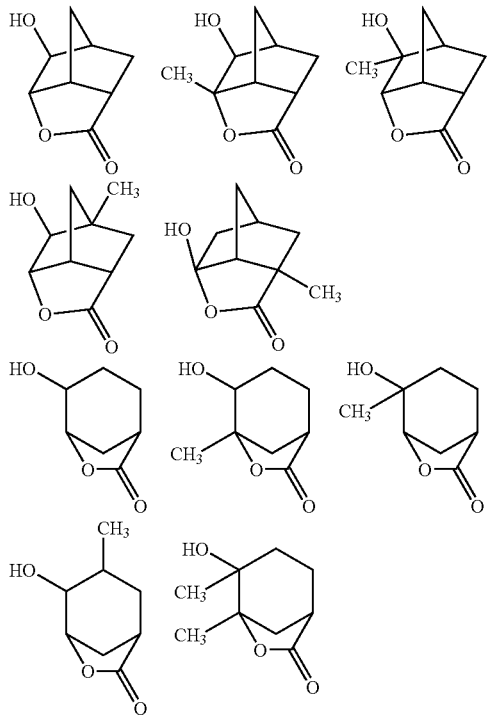

Examples of the acryloyloxy-γ-butyrolactone and the methacryloyloxy-γ-butyrolactone in which lactone ring may be substituted with the alkyl group include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone and β-methacryloyloxy-α-methyl-γ-butyrolactone.

The resin containing a structural unit derived from 2-norbornene shows strong structure because the alicyclic group is directly present on its main chain and shows a property that dry etching resistance is excellent. The structural unit derived from 2-norbornene can be introduced into the main chain by radical polymerization using, for example, an aliphatic unsaturated dicarboxylic anhydride such as maleic anhydride and itaconic anhydride together in addition to corresponding 2-norbornene. The structural unit derived from 2-norbornene is formed by opening of its double bond, and can be represented by the above-mentioned formula (c). The structural units derived from maleic anhydride and from itaconic anhydride which are the structural unit derived from aliphatic unsaturated dicarboxylic anhydrides are formed by opening of their double bonds, and can be represented by the above-mentioned formula (d) and the formula (e), respectively.

In $R^{15}$ and $R^{16}$, examples of the C1-C3 alkyl group include a methyl group, an ethyl group, and a propyl group, and examples of the C1-C3 hydroxyalkyl group include a hydroxymethyl group and a 2-hydroxyethyl group.

In $R^{15}$ and $R^{16}$, the —COOU group is an ester formed from the carboxyl group, and examples of the alcohol residue corresponding to U include an optionally substituted C1-C8 alkyl group, 2-oxooxolan-3-yl group and 2-oxooxolan-4-yl group, and examples of the substituent on the C1-C8 alkyl group include a hydroxyl group and an alicyclic hydrocarbon group.

Specific examples of the monomer used to give the structural unit represented by the above-mentioned formula (c) may include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When U in the —COOU group is the acid-labile group, the structural unit represented by the formula (c) is a structural unit having the acid-labile group even if it has the norbornane structure. Examples of monomers giving a structural unit having the acid-labile group include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

The content of the structural unit having an acid-labile group in the resin is usually 10 to 80% by mole based on total molar of all the structural units of the resin.

In the photoresist composition, the content of the resin is usually 70 to 99.9% by weight and preferably 80 to 95% by weight based on the amount of solid components, and the content of the acid generator components is usually 0.1 to 30% by weight and preferably 5 to 20% by weight based on the amount of solid components.

Herein, "solid components" means sum of components other than a solvent(s) in the photoresist composition, and "acid generator components" means the sulfonium compound (Ia) and the other acid generator(s).

In the photoresist composition, performance deterioration caused by inactivation of acid which occurs due to post exposure delay can be diminished by adding an organic base compound, particularly a nitrogen-containing organic base compound as a quencher.

Specific examples of the nitrogen-containing organic base compound include nitrogen-containing organic base compounds represented by the following formulae:

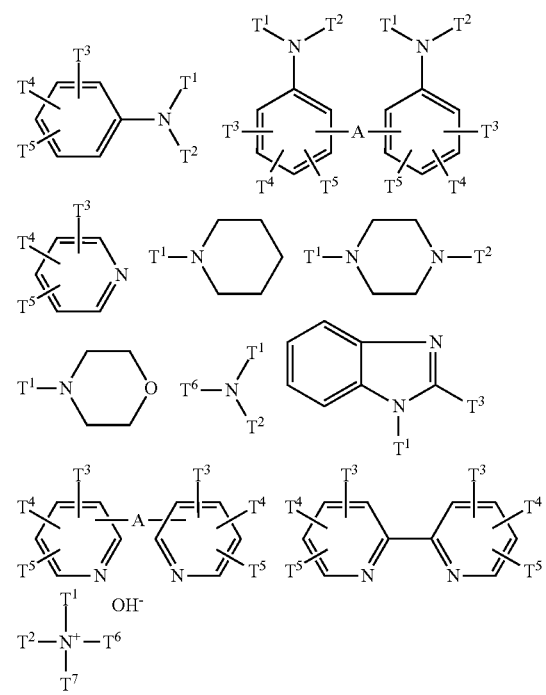

wherein $T^1$, $T^2$ and $T^7$ each independently represent a hydrogen atom, a C1-C6 aliphatic hydrocarbon group, a C5-C10 alicyclic hydrocarbon group or a C6-C20 aromatic hydrocarbon group, and the aliphatic hydrocarbon group, the alicyclic hydrocarbon group and the aromatic hydrocarbon group may have one or more groups selected from the group consisting of a hydroxyl group, an amino group which may be substituted with a C1-C4 aliphatic hydrocarbon group and a C1-C6 alkoxy group, $T^3$, $T^4$ and $T^5$ each independently represent a hydrogen atom, a C1-C6 aliphatic hydrocarbon group, a C5-C10 alicyclic hydrocarbon group, a C6-C20 aromatic hydrocarbon group or a C1-C6 alkoxy group, and the aliphatic hydrocarbon group, the alicyclic hydrocarbon group, the aromatic hydrocarbon group and the alkoxy group may have one or more groups selected from the group consisting of a hydroxyl group, an amino group which may be substituted with a C1-C4 aliphatic hydrocarbon group and a C1-C6 alkoxy group, $T^6$ represents a C1-C6 aliphatic hydrocarbon group or a C5-C10 alicyclic hydrocarbon group, and the aliphatic hydrocarbon group and the alicyclic hydrocarbon group may have one or more groups selected from the group consisting of a hydroxyl group, an amino group which may be substituted with a C1-C4 aliphatic hydrocarbon group and a C1-C6 alkoxy group, and A represents —CO—, —NH—, —S—, —S—S— or a C2-C6 alkylene group, Examples of the amino group which may be substituted with the C1-C4 aliphatic hydrocarbon group include an amino group, a methylamino group, an ethylamino group, a butylamino group, a dimethylamino group and a diethylamino group. Examples of the C1-C6 alkoxy group include a methoxy group, an ethoxy group, a propoxy group, an isopropoxy group, a butoxy group, a tert-butoxy group, a pentyloxy group, a hexyloxy group and a 2-methoxyethoxy group.

Specific examples of the aliphatic hydrocarbon group which may have one or more groups selected from the group consisting of a hydroxyl group, an amino group which may be substituted with a C1-C4 aliphatic hydrocarbon group, and a C1-C6 alkoxy group include a methyl group, an ethyl group, a propyl group, an isopropyl group, a butyl group, a tert-butyl group, a pentyl group, a hexyl group, an octyl group, a nonyl group, a decyl group, a 2-(2-methoxyethoxy)ethyl group, a 2-hydroxyethyl group, a 2-hydroxypropyl group, a 2-aminoethyl group, a 4-aminobutyl group and a 6-aminohexyl group.

Specific examples of the alicyclic hydrocarbon group which may have one or more groups selected from the group consisting of a hydroxyl group, an amino group which may be substituted with a C1-C4 aliphatic hydrocarbon group and a C1-C6 alkoxy group include a cyclopentyl group, a cyclohexyl group, a cycloheptyl group and a cyclooctyl group.

Specific examples of the aromatic hydrocarbon group which may have one or more groups selected from the group consisting of a hydroxyl group, an amino group which may be substituted with a C1-C4 aliphatic hydrocarbon group and a C1-C6 alkoxy group include a phenyl group and naphthyl group.

Specific examples of the alkoxy group include a methoxy group, an ethoxy group, a propoxy group, an isopropoxy group, a butoxy group, a tert-butoxy group, a pentyloxy group and a hexyloxy group. Specific examples of the alkylene group include an ethylene group, a trimethylene group, a tetramethylene group, a methylenedioxy group and an ethylene-1,2-dioxy group.

Specific examples of the nitrogen-containing organic base compounds include hexylamine, heptylamine, octylamine, nonylamine, decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di (2-pyridyl)ethane, 1,2-di(4-pyridyl)ethane, 1,3-di(4-pyridyl) propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine, 3,3'-dipicolylamine, tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl) trimethylammonium hydroxide and (2-hydroxyethyl) trimethylammonium hydroxide (so-called "choline").

A hindered amine compound having a piperidine skelton as disclosed in JP 11-52575 A1 can be also used as the quencher.

In the point of forming patterns having higher resolution, the quaternary ammonium hydroxide is preferably used as the quencher.

When the basic compound is used as the quencher, the present resist composition preferably includes 0.01 to 1% by weight of the basic compound and more preferably includes 0.05 to 0.3% by weight of the basic compound based on the total amount of the solid components.

The photoresist composition can contain, if necessary, a small amount of various additives such as a sensitizer, a dissolution inhibitor, other polymers, a surfactant, a stabilizer and a dye as long as the effect of the present invention is not prevented.

The photoresist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A resist film applied onto the substrate and then dried is subjected to exposure for patterning, then heat-treated to facilitate a deblocking reaction, and thereafter developed with an alkali developer. The alkali developer used may be any one of various alkaline aqueous solution used in the art. Generally, an aqueous solution of tetramethylammonium hydroxide or (2-hydroxyethyl)trimethylammonium hydroxide (commonly known as "choline") is often used.

It should be construed that embodiments disclosed here are examples in all aspects and not restrictive. It is intended that the scope of the present invention is determined not by the above descriptions but by appended claims, and includes all variations of the equivalent meanings and ranges to the claims.

The present invention will be described more specifically by Examples, which are not construed to limit the scope of the present invention. The "%" and "part(s)" used to represent the content of any compound and the amount of any material to be used in the following Examples are on a weight basis unless otherwise specifically noted. Structures of compounds obtained were determined by NMR (EX-270 Type manufactured by JEOL LTD.) and mass spectrometry (Liquid Chromatography: 1100 Type manufactured by AGILENT TECHNOLOGIES LTD., Mass Spectrometry: LC/MSD Type or LC/MSD TOF Type manufactured by AGILENT TECHNOLOGIES LTD.).

EXAMPLE 1

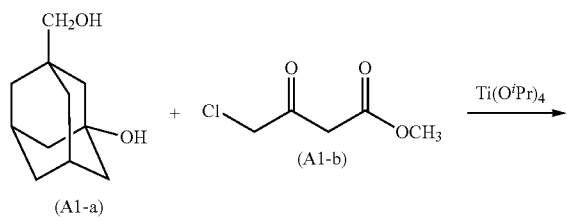

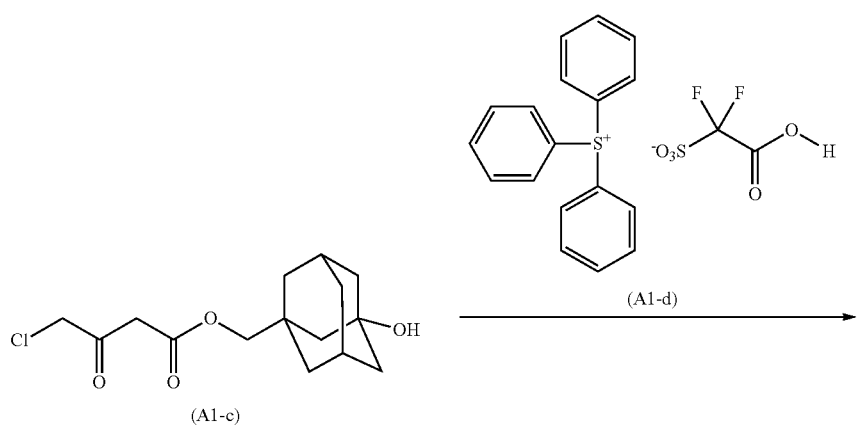

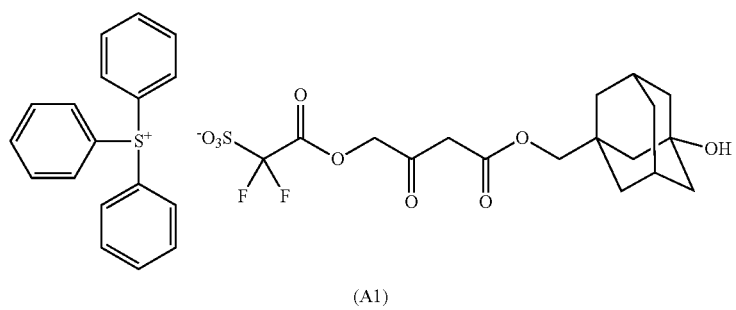

(1) To a solution of 5 parts of a compound represented by the formula (A1-a), 25 parts of toluene and 25 parts of dichloroethane, 4.1 parts of a compound represented by the formula (A1-b) and 0.34 part of titanium tetraisopropoxide were added. The resultant mixture was refluxed for 22 hours. The obtained reaction mixture was cooled down to room temperature and 125 parts of ion-exchanged water was added thereto. The obtained mixture was extracted with 200 parts of chloroform. The obtained organic layer was washed three times with water and then concentrated under reduced pressure to obtain 7.8 parts of a compound represented by the formula (A1-c).

$^1$H-NMR (dimethylsulfoxide-$d_6$): δ (ppm) 4.60 (2H, s), 4.41 (1H, brs), 3.72 (4H, s), 2.09 (2H, s), 1.58-1.26 (12H, m) MS (ESI (+) Spectrum): [M+Na]$^+$ 323.1 ($C_{15}H_2Cl_2NO_5S$=300.1)

(2) To a solution of 5.8 parts of a compound represented by the formula (A1-d) and 29 parts of N,N-dimethylformamide, 1.8 parts of potassium carbonate and 0.25 part of potassium iodide were added.

The resultant mixture was stirred at 40° C. for 1 hour, and then, 4 parts of a compound represented by the formula (A1-c) and 8 parts of N,N-dimethylformamide were added thereto. The obtained mixture was stirred at 40° C. for 6 hours. To the obtained reaction mixture, 5% aqueous oxalic acid solution was added followed by conducting extraction with chloroform. The obtained organic layer was washed with ion-exchanged water and then, concentrated under reduced pressure to obtain 2.1 parts of a compound represented by the formula (A1).

$^1$H-NMR (dimethylsulfoxide-$d_6$): δ (ppm) 7.91-7.70 (15H, m), 5.06 (2H, s), 4.40 (1H, brs), 3.71 (4H, m), 2.09 (2H, s), 1.61-1.23 (12H, m)

EXAMPLE 2

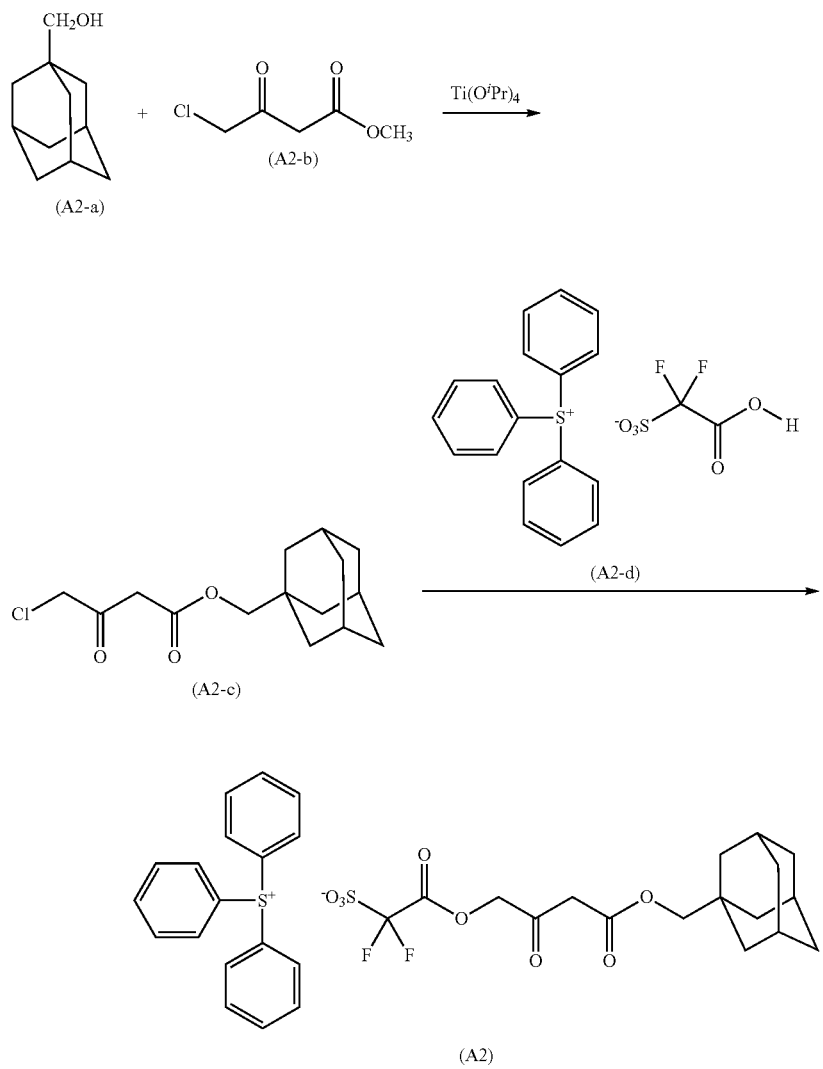

(1) To a solution of 5 parts of a compound represented by the formula (A2-a) and 50 parts of toluene, 4.5 parts of a compound represented by the formula (A2-b) and 0.37 part of titanium tetraisopropoxide were added. The resultant mixture was refluxed for 22 hours. The obtained reaction mixture was cooled down to room temperature and 50 parts of saturated aqueous tartaric acid solution was added thereto. The obtained mixture was extracted with 200 parts of chloroform. The obtained organic layer was washed three times with water and then concentrated under reduced pressure to obtain 7.8 parts of a compound represented by the formula (A2-c).

$^1$H-NMR (dimethylsulfoxide-$d_6$): δ (ppm) 4.60 (2H, s), 3.72 (2H, s), 3.67 (2H, s), 1.98-1.88 (3H, brm), 1.74-1.39 (12H, m)

(2) To a solution of 5.4 parts of a compound represented by the formula (A2-d) and 27 parts of N,N-dimethylformamide, 1.7 parts of potassium carbonate and 0.5 part of potassium iodide were added. The resultant mixture was stirred at 40° C. for 1 hour, and then, 4 parts of a compound represented by the formula (A2-c) and 7 parts of N,N-dimethylformamide were added thereto. The obtained mixture was stirred at 40° C. for 5 hours. To the obtained reaction mixture, 5% aqueous oxalic acid solution was added followed by conducting extraction with chloroform. The obtained organic layer was washed with ion-exchanged water and then, concentrated under reduced pressure to obtain 2.4 parts of a compound represented by the formula (A2).

$^1$H-NMR (dimethylsulfoxide-$d_6$): δ (ppm) 7.91-7.70 (15H, m), 5.06 (2H, s), 3.71 (2H, s), 3.67 (2H, s), 1.97-1.87 (3H, m), 1.72-1.52 (6H, m), 1.51-1.44 (6H, m)

EXAMPLE 3

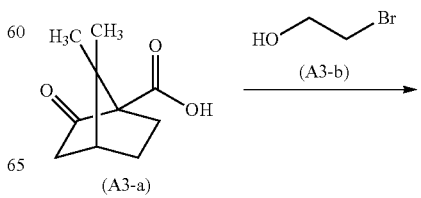

-continued

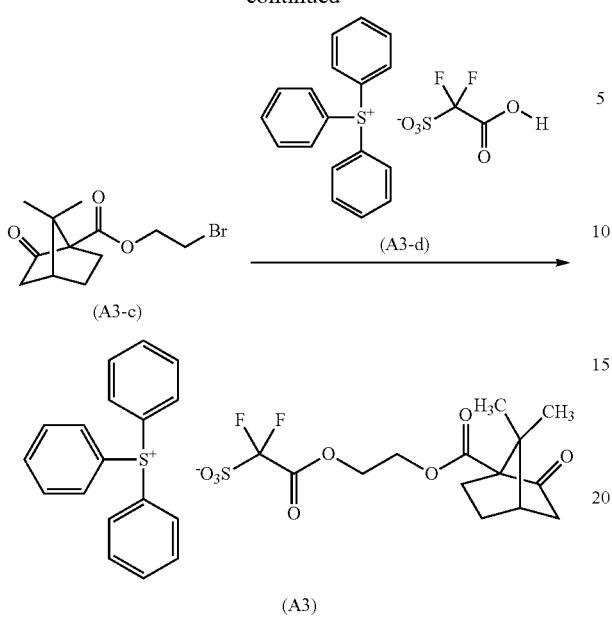

(1) To a solution of 5 parts of a compound represented by the formula (A3-a) and 50 parts of monochlorobutane, 4.1 parts of a compound represented by the formula (A3-b) and 0.05 part of sulfuric acid were added. The resultant mixture was refluxed for 3 hours. The obtained reaction mixture was cooled down to room temperature and 50 parts of saturated aqueous sodium hydrogen carbonate solution was added thereto. The obtained mixture was extracted with 100 parts of ethyl acetate. The obtained organic layer was washed three times with water and then concentrated under reduced pressure to obtain 6.5 parts of a compound represented by the formula (A3-c).

(2) To a solution of 7.6 parts of a compound represented by the formula (A3-d) and 38 parts of N,N-dimethylformamide, 2.3 parts of potassium carbonate and 0.7 part of potassium iodide were added.

The resultant mixture was stirred at 40° C. for 1 hour, and then, a solution of 5 parts of a compound represented by the formula (A3-c) and 7 parts of N,N-dimethylformamide was added thereto. The obtained mixture was stirred at 40° C. for 5 hours. To the obtained reaction mixture, 5% aqueous oxalic acid solution was added followed by conducting extraction with chloroform. The obtained organic layer was washed with ion-exchanged water and then, concentrated under reduced pressure to obtain 7.8 parts of a compound represented by the formula (A3).

MS (ESI(+) Spectrum): M$^+$ 263.1 ($C_{18}H_{15}S^+$=263.1)

MS (ESI(−) Spectrum): M$^-$ 383.1 ($C_{14}H_{17}F_2O_8S^-$=383.1)

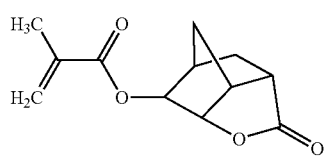

(E1)

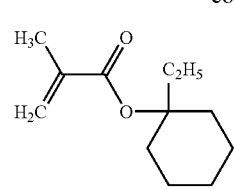

(E2)

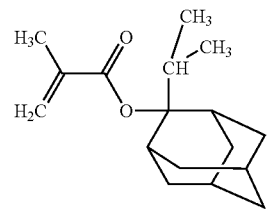

(E3)

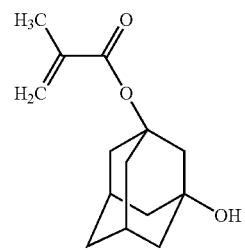

(E4)

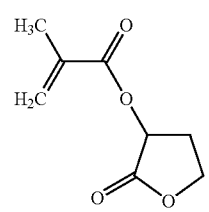

(E5)

RESIN SYNTHESIS EXAMPLE 1

Into a four-necked flask equipped with a condenser, a stirrer and a thermometer, 29.6 parts of 1,4-dioxane was added, and then heated to 73° C. A solution prepared by mixing 12.8 parts of monomer E1, 6.0 parts of monomer E2, 16.0 parts of monomer E3, 3.1 parts of monomer E4, 11.5 parts of monomer E5, 0.36 part of 2,2'-azobisisobutyronitrile, 1.62 part of 2,2'-azobis (2,4-dimethylvaleronitrile) and 44.4 parts of 1,4-dioxane was added dropwise thereto over 2 hours. The resultant mixture was heated at 73° C. for 5 hours. The reaction mixture was cooled down to room temperature and then pored into a mixed solution of 128 parts of water and 514 parts of methanol to cause precipitation.

The precipitate was isolated and washed with methanol followed by drying under reduced pressure to obtain a resin having a weight-average molecular weight of 8,900 and degree of dispersion (Mw/Mn) of 1.6. This resin had the following structural units.

This is called as resin B1.

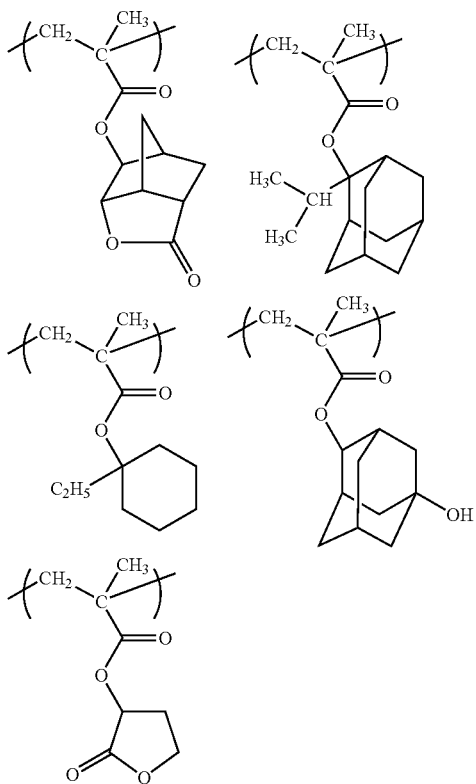

EXAMPLES 4 TO 6 AND COMPARATIVE EXAMPLE 1

Acid Generator

A1: a compound represented by the formula (A1)
A2: a compound represented by formula (A2)
A3: a compound represented by formula (A3)
C1: a compound represented by formula (C1)

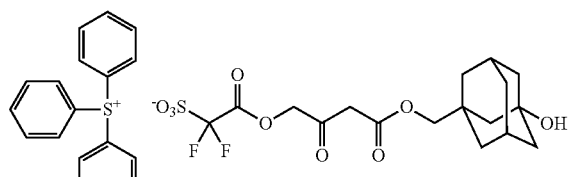
(A1)

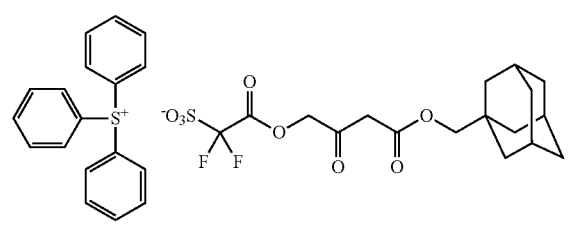
(A2)

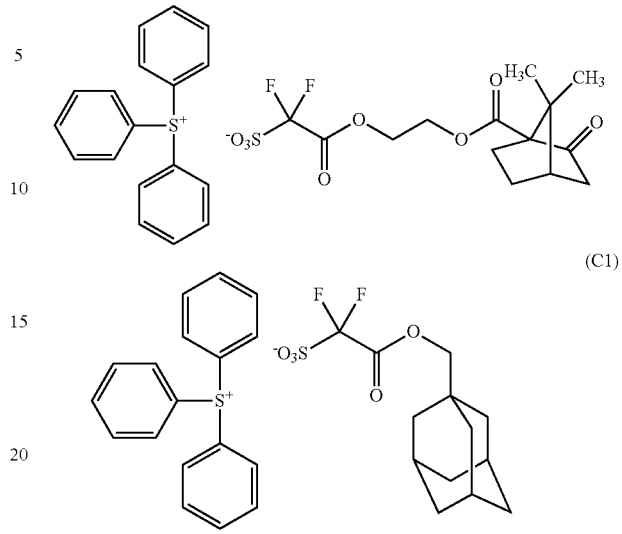

<Resin>
B1: Resin B1
<Basic Compound>
Q1: 2,6-diisopropylaniline
<Solvent>

| Y1: | propylene glycol monomethyl ether | 145 parts |
| | 2-heptanone | 20 parts |
| | propylene glycol monomethyl ether acetate | 20 parts |
| | γ-butyrolactone | 3.5 parts |

The following components were mixed and dissolved, further, filtrated through a fluorine resin filter having pore diameter of 0.2 μm, to prepare resist compositions.
Resin (kind and amount are described in Table 1)
Acid generator (kind and amount are described in Table 1)
Basic compound (kind and amount are described in Table 1)
Solvent (kind is described in Table 1)
Silicon wafers were each coated with "ARC-95", which is an organic anti-reflective coating composition available from Nissan Chemical Industries, Ltd., and then baked at 205° C. for 60 seconds, to form a 78 nm-thick organic anti-reflective coating. Each of the resist compositions prepared as above was spin-coated over the anti-reflective coating so that the thickness of the resulting film became 110 nm after drying. The silicon wafers thus coated with the respective resist liquids were each prebaked on a proximity hotplate at 100° C. for 60 seconds. Using an ArF excimer stepper ("FPA-5000AS3" manufactured by CANON INC., NA=0.75, 2/3 Annular), each wafer thus formed with the respective resist film was subjected to line and space pattern exposure, with the exposure quantity being varied stepwise.
After the exposure, each wafer was subjected to post-exposure baking on a hotplate at 100° C. for 60 seconds and then to paddle development for 15 seconds with an aqueous solution of 2.38 wt % tetramethylammonium hydroxide at 23° C.
Each of a dark field pattern developed on the organic anti-reflective coating substrate after the development was observed with a scanning electron microscope ("S-4100" manufactured by Hitachi, Ltd.), the results of which are shown in Table 2. The term "dark field pattern", as used herein, means a pattern obtained by exposure and development through a reticle comprising chromium base surface (light-shielding portion) and linear glass layers (light-transmitting portion) formed in the chromium surface and aligned with each other. Thus, the dark field pattern is such that, after exposure and development, resist layer surrounding the line and space pattern remains on substrate.

Resolution: Photoresist patterns which gave the space pattern split by the line pattern at the exposure amount that the line pattern and the space pattern become 1:1 after exposure through 85 nm line and space pattern mask and development were observed with a scanning electron microscope. Resolution is expressed as the minimum size of space pattern which gave the space pattern split by the line pattern at the above exposure amount.

Exposure margin: Photoresist patterns which gave the space pattern split by the line pattern at the exposure amount that the line pattern and the space pattern become 1:1 after exposure through 85 nm line and space pattern mask and development were observed with a scanning electron microscope. Line widths of the obtained patterns were plotted against exposure amounts on forming the pattern to make a graph wherein a horizontal axis is an exposure amount and a vertical axis is a line width of the pattern. When a slope of the plotted line is smaller than that of Comparative Example 1, exposure margin is good and its evaluation is marked by "○" and when a slope of the plotted line is bigger than that of Comparative Example 1, exposure margin is bad and its evaluation is marked by "×".

TABLE 1

| Ex. No. | Resin (kind/amount (part)) | Acid generator (kind/amount (part)) | Basic compound (kind/amount (part)) | Solvent |
|---|---|---|---|---|
| Ex. 4 | B1/10 | A1/1.4 | Q1/0.14 | Y1 |
| Ex. 5 | B1/10 | A2/1.1 | Q1/0.14 | Y1 |
| Ex. 6 | B1/10 | A3/1.2 | Q1/0.14 | Y1 |
| Comp. Ex. 1 | B1/10 | C1/0.98 | Q1/0.14 | Y1 |

TABLE 2

| Ex. No. | Resolution (nm) | Exposure margin |
|---|---|---|
| Ex. 4 | 75 | ○ |
| Ex. 5 | 75 | ○ |
| Ex. 6 | 75 | ○ |
| Comp. Ex. 1 | 75 | — |

The sulfonium compound represented by the formula (Ia) is suitably used for an acid generator capable of providing chemically amplified positive photoresist compositions.

What is claimed is:

1. A sulfonium compound represented by the formula (I):

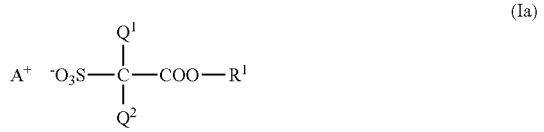

(Ia)

wherein $Q^1$ and $Q^2$ each independently represent a fluorine atom or a C1-C6 perfluoroalkyl group, R1 represents a C5-C42 organic group having a β-ketoester structure and $A^+$ represents an organic counter ion.

2. The sulfonium compound according to claim 1, wherein $R^1$ is a group represented by the formula (Ib):

wherein $R^2$ represents a C1-C12 divalent hydrocarbon group and $R^3$ represents a C1-C24 hydrocarbon group which may have one or more substituents, and —CH$_2$— in the C1-C24 hydrocarbon group may be replaced by —NH—, —CO— or —O—, and —CH= in the C1-C24 hydrocarbon group may be replaced by —NH=.

3. The sulfonium compound according to claim 2, wherein $R^2$ is a methylene group, an ethylene group, a trimethylene group or a tetramethylene group.

4. The sulfonium compound according to claim 2, wherein the substituent in $R^3$ is a halogen atom, a hydroxyl group, a cyano group, —OR$^4$—, —CO—OR$^4$, —O—CO—R$^4$, —SO$_2$R$^4$ or —O—SO$_2$—R$^4$ wherein R$^4$ represents a C1-C6 hydrocarbon group.

5. The sulfonium compound according to claim 1, wherein $Q^1$ and $Q^2$ each independently represent a fluorine atom or a trifluoromethyl group.

6. The sulfonium compound according to claim 1, wherein the organic counter ion is a cation represented by the formula (IXz):

wherein $P^a$, $P^b$ and $P^c$ each independently represent a C1-C30 alkyl group which may be substituted with at least one selected from the group consisting of a hydroxyl group, a C1-C12 alkoxy group and a C3-C12 cyclic hydrocarbon group, or a C3-C30 cyclic hydrocarbon group which may be substituted with at least one selected from the group consisting of a hydroxyl group, a halogen atom and a C1-C12 alkoxy group.

7. The sulfonium compound according to claim 1, wherein the organic counter ion is a cation represented by the formula (IIIa):

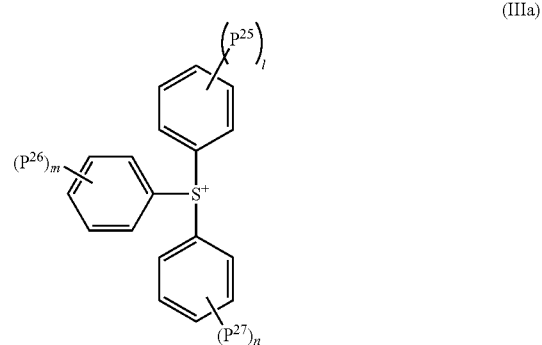

wherein $P^{25}$, $P^{26}$ and $P^{27}$ are independently in each occurrence a hydroxyl group, a halogen atom, a C1-C12 alkyl group, a C1-C12 alkoxy group or a C3-C12 cyclic hydrocarbon group, and the C3-C12 cyclic hydrocarbon group may be substituted with a halogen atom, a hydroxyl group or a C1-C12 alkoxy group, and l, m and n each independently represent an integer of 0 to 5.

8. A chemically amplified photoresist composition comprising a sulfonium compound according to claim 1 and a resin comprising a structural unit having an acid-labile group and being insoluble or poorly soluble in an aqueous alkali solution but becoming soluble in an aqueous alkali solution by the action of an acid.

9. The chemically amplified photoresist composition according to claim 8, wherein the composition further contains a basic compound.

10. A process for production of a sulfonium compound represented by the formula (Ia):

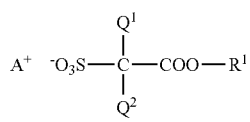
(Ia)

wherein $Q^1$ and $Q^2$ each independently represent a fluorine atom or a C1-C6 perfluoroalkyl group, R1 represents a C5-C42 organic group having a β-ketoester structure and $A^+$ represents an organic counter ion, which comprises reacting a compound represented by the formula (VI):

Z—R$^1$     (VI)

wherein $R^1$ is the same as defined above, and Z represents a halogen atom, with a salt represented by the formula (VII):

(VII)
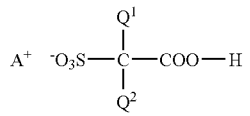

wherein $Q^1$, $Q^2$ and $A^+$ are the same as defined above.

11. A process for production of a sulfonium compound represented by the formula (Ia):

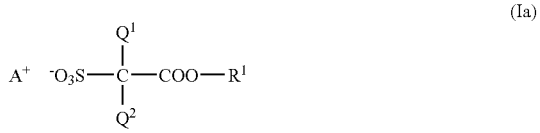
(Ia)

wherein $Q^1$ and $Q^2$ each independently represent a fluorine atom or a C1-C6 perfluoroalkyl group, R1 represents a C5-C42 organic group having a β-ketoester structure and $A^+$ represents an organic counter ion, which comprises reacting a compound represented by the formula (VIII):

A$^+$L$^-$     (VIII)

wherein $A^+$ is the same as defined above, and $L^-$ represents $F^-$, $Cl^-$, $Br^-$, $I^-$, $BF_4^-$, $AsF_6^-$, $SbF_6^-$, $PF_6^-$ or $ClO_4^-$, with a salt represented by the formula (IX):

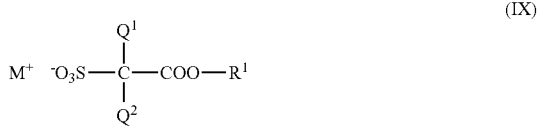
(IX)

wherein $Q^1$, $Q^2$ and $R^1$ are the same as defined above and $M^+$ is $Li^+$, $Na^+$ or $K^+$.

* * * * *